US009364569B2

(12) United States Patent
Schneider et al.

(10) Patent No.: US 9,364,569 B2
(45) Date of Patent: Jun. 14, 2016

(54) ULTRASOUND CONTRAST AGENTS AND PROCESS FOR THE PREPARATION THEREOF

(75) Inventors: Michel Schneider, Troinex (CH); Philippe Bussat, Feigeres (FR); Feng Yan, Grand Lancy (CH); Christian Guillot, Beaumont (FR)

(73) Assignee: Bracco Suisse S.A., Manno (CH)

( * ) Notice: Subject to any disclaimer, the term of this patent is extended or adjusted under 35 U.S.C. 154(b) by 2463 days.

(21) Appl. No.: 10/544,123

(22) PCT Filed: Feb. 3, 2004

(86) PCT No.: PCT/IB2004/000243
§ 371 (c)(1),
(2), (4) Date: Aug. 2, 2005

(87) PCT Pub. No.: WO2004/069284
PCT Pub. Date: Aug. 19, 2004

(65) Prior Publication Data
US 2006/0051297 A1    Mar. 9, 2006

(30) Foreign Application Priority Data
Feb. 4, 2003 (EP) ..................................... 03002375

(51) Int. Cl.
*A61K 49/22* (2006.01)
(52) U.S. Cl.
CPC ................................... *A61K 49/223* (2013.01)
(58) Field of Classification Search
CPC .................................................. A61K 49/223
USPC ....................................... 424/9.5, 9.51, 9.52
See application file for complete search history.

(56) References Cited

U.S. PATENT DOCUMENTS

| | | |
|---|---|---|
| 4,276,885 A | 7/1981 | Tickner et al. |
| 4,675,381 A | 6/1987 | Bichon |
| 4,888,398 A | 12/1989 | Bichon et al. |
| 4,892,733 A | 1/1990 | Bichon et al. |
| 5,271,928 A | 12/1993 | Schneider et al. |
| 5,413,774 A | 5/1995 | Schneider et al. |
| 5,445,813 A | 8/1995 | Schneider et al. |
| 5,487,390 A | 1/1996 | Cohen et al. |
| 5,531,980 A | 7/1996 | Schneider et al. |
| 5,545,395 A | 8/1996 | Tournier et al. |
| 5,556,610 A | 9/1996 | Yan et al. |
| 5,562,099 A | 10/1996 | Cohen et al. |
| 5,597,549 A | 1/1997 | Schneider et al. |
| 5,605,673 A | 2/1997 | Schutt et al. |
| 5,626,867 A | 5/1997 | Eibl et al. |
| 5,711,933 A | 1/1998 | Bichon et al. |
| 5,733,572 A | 3/1998 | Unger et al. |
| 5,741,522 A | 4/1998 | Violante et al. |
| 5,827,504 A | 10/1998 | Yan et al. |
| 5,985,247 A | 11/1999 | Soetanto |
| 6,139,818 A | 10/2000 | Bichon et al. |
| 6,139,819 A | 10/2000 | Unger et al. |
| 6,146,657 A | 11/2000 | Unger et al. |
| 6,153,172 A | 11/2000 | Schroder |
| 6,165,442 A | 12/2000 | Swaerd-Nordmo et al. |
| 6,183,725 B1 | 2/2001 | Yan et al. |
| 6,221,337 B1 | 4/2001 | Dugstad et al. |
| 6,245,318 B1 | 6/2001 | Klianov et al. |
| 6,258,378 B1 | 7/2001 | Schneider et al. |
| 6,280,705 B1 | 8/2001 | Trevino et al. |
| 6,309,665 B2 | 10/2001 | Barthelemy et al. |
| 6,331,289 B1 | 12/2001 | Klavemess et al. |
| 6,333,021 B1 | 12/2001 | Schneider et al. |
| 6,375,931 B2 | 4/2002 | Ostensen et al. |
| 6,416,740 B1 | 7/2002 | Unger |
| 6,576,220 B2 | 6/2003 | Unger |
| 6,793,626 B2 | 9/2004 | Tsuzuki |
| 7,083,572 B2 | 8/2006 | Unger et al. |
| 9,248,204 B2 | 2/2016 | Bussat et al. |
| 2002/0102216 A1 | 8/2002 | Lanza et al. |
| 2002/0102217 A1 | 8/2002 | Klaveness et al. |
| 2002/0159952 A1 | 10/2002 | Unger |
| 2002/0169138 A1 | 11/2002 | Kunz et al. |
| 2004/0146462 A1 | 7/2004 | Eriksen et al. |
| 2005/0130167 A1 | 6/2005 | Bao et al. |

FOREIGN PATENT DOCUMENTS

| | | | |
|---|---|---|---|
| EP | 0130935 A1 | 1/1985 | |
| EP | 0324938 A1 | 7/1989 | |

(Continued)

OTHER PUBLICATIONS

PCT Written Opinion of the International Searching Authority, Oct. 19, 2004, European Patent Office, Munich, Germany.
PCT International Preliminary Report on Patentability, Chapter I, Aug. 5, 2005, The International Bureau of WIPO, Geneva Switzerland.
Goertz, D.E. et al., "Effect of Bubble Size Distribution on Nonlinear Scattering from Microbubbles at High Frequencies", IEEE Ultrasonics Symposium Poster Session, 2003, p. 229.
Goertz, D.E. et al., "The Effect of Bubble Size on Nonlinear Scattering From Microbubbles at High Frequencies", IEEE Ultrasonics Symposium, 2003, pp. 1503-1506.
Halpern, Ethan et al., "Directed Biopsy During Contrast-Enhanced Sonography of the Prostate", AJR, vol. 178, 2002, pp. 915-919.

(Continued)

*Primary Examiner* — Michael G Hartley
*Assistant Examiner* — Leah Schlientz
(74) *Attorney, Agent, or Firm* — Vivicar Law, PLLC

(57) ABSTRACT

Method for preparing a lyophilized matrix and, upon reconstitution of the same, a respective injectable contrast agent comprising a liquid aqueous suspension of gas-filled microbubbles stabilized predominantly by a phospholipid. The method comprises preparing an emulsion from an aqueous medium, a phospholipid and a water immiscible organic solvent. The emulsion is then freeze-dried and subsequently reconstituted in an aqueous suspension of gas-filled microbubbles. The method allows to obtain suspensions comprising microbubbles having a relatively small diameter and a narrow size distribution.

57 Claims, No Drawings

(56) References Cited

FOREIGN PATENT DOCUMENTS

| | | |
|---|---|---|
| EP | 0554213 A1 | 8/1993 |
| EP | 0558748 A1 | 9/1993 |
| EP | 1 228 770 A1 | 8/2002 |
| EP | 0804251 B1 | 9/2002 |
| EP | 1 419 789 A2 | 5/2004 |
| JP | H07-503976 A | 4/1995 |
| JP | 2000-143550 A | 5/2000 |
| JP | 2001-508454 A | 6/2001 |
| JP | 2001-511765 A | 8/2001 |
| JP | 2001-524983 A | 12/2001 |
| JP | 2002-502829 A | 1/2002 |
| JP | 2002-512206 A | 4/2002 |
| JP | 2002-212108 A | 7/2002 |
| JP | 2002-522379 A | 7/2002 |
| JP | 2007-515470 A | 6/2007 |
| JP | 2007-515471 A | 6/2007 |
| WO | 87/03891 A1 | 7/1987 |
| WO | WO 91/15244 | 10/1991 |
| WO | 92/09829 A1 | 6/1992 |
| WO | WO 94/01140 * | 1/1994 ............. A61K 49/00 |
| WO | 94/04197 A1 | 3/1994 |
| WO | WO 94/09829 | 5/1994 |
| WO | 94/28873 A1 | 12/1994 |
| WO | 95/23615 A1 | 9/1995 |
| WO | 96/07434 A1 | 3/1996 |
| WO | WO 96/09037 | 3/1996 |
| WO | 97/29782 A1 | 8/1997 |
| WO | WO 97/29783 | 8/1997 |
| WO | WO 97/40858 | 11/1997 |
| WO | 98/04074 A1 | 1/1998 |
| WO | WO 98/05364 | 2/1998 |
| WO | 98/18500 A2 | 5/1998 |
| WO | 98/18501 A2 | 5/1998 |
| WO | 98/32468 A1 | 7/1998 |
| WO | WO 98/42383 A1 | 10/1998 |
| WO | WO 98/42384 A1 | 10/1998 |
| WO | 98/51284 A1 | 11/1998 |
| WO | WO 99/08716 | 2/1999 |
| WO | WO 99/20312 A1 | 4/1999 |
| WO | WO 99/36104 | 7/1999 |
| WO | 99/39738 A1 | 8/1999 |
| WO | 99/53963 A1 | 10/1999 |
| WO | WO 99/53963 A1 | 10/1999 |
| WO | 99/55383 A2 | 11/1999 |
| WO | 01/68150 A1 | 9/2001 |
| WO | WO 02/055544 | 7/2002 |
| WO | 03/005029 A2 | 1/2003 |
| WO | 03/015831 A1 | 2/2003 |
| WO | 03/074005 A2 | 9/2003 |
| WO | 03/084574 A1 | 10/2003 |
| WO | 2004/001140 A1 | 12/2003 |
| WO | 2004/069284 A2 | 8/2004 |
| WO | 2005/063305 A1 | 7/2005 |
| WO | 2005/063306 A1 | 7/2005 |
| WO | WO2005/070472 A2 | 8/2005 |

OTHER PUBLICATIONS

Michel Schneider et al: "BR1: A New Ultrasonographic Contrast Agent Based on Sulfur Hexafluoride-Filled Microbubbles" Investigative Radiology, vol. 30, No. 8, pp. 451-457, XP611270, 1995.
Simon Lockyer et al: "Demonstration of Flow and Platelet Dependency in a Ferric Chloride-Induced Model of Thrombosis" Journal of Cardiovascular Pharmacology, vol. 33, No. 5, pp. 718-725, 1999.
Erika Bohl Kullberg et al: "Development of EGF-Conjugated Liposomes for Targeted Delivery of Boronated DNA-Binding Agent" Bioconjugate Chem. vol. 13, No. 4; pp. 737-743, 2002.
Brian C. Eatock et al: "Numerical studies of the spectrum of low-intensity ultrasound scattered by bubbles" J. Acoust. Soc. Am., vol. 77, No. 5, pp. 1692-1701, 1985.
Yekta Ozer et al: Influence of Freezing and Freeze-Drying on the Stability of Liposomes Dispersed in Aqueous Media, Acta Pharm. Technol., 1988, pp. 129-139, vol. 34, No. 3, pp. 129-139.
Martin MacPinsten: "Surfactants and Polymers in Drug Delivery" Marcel Dekker, pp. 56-60, 2002.
Matthew J. Hasik et al: "Evaluation of synthetic phospholipids ultrasound contrast agents", Ultrasonics, 2002, pp. 973-982, Elsevier Science B.V., New York, N.Y.
PCT Search Report for PCT/IB2004/000243, mail date Sep. 22, 2004.
First Office Action for Chinese application No. 201310032548.X, mail date Feb. 17, 2014 (English translation).
Second Office Action for Chinese application No. 201310032548.X, mail date Dec. 22, 2014 (English translation).
De Jong, N. et al: "Absorption and scatter of encapsulated gas filled microspheres: theoretical considerations and some measurements", Ultrasonics, XP-00267462, Mar. 1992, pp. 95-103, vol. 30, No. 2, Butterworth-Heinemann Ltd., Guildford, Surrey, Great Britain.
Edited by R. R. C. New "Liposomes, a practical approach", 1989, pp. 45-55, Oxford University Press, Oxford, New York, Tokyo.
Gorce et al., "Influence of Bubble Size Distribution on the Echogenicity of Ultrasound Contrast Agents A Study of SonoVue", Investigative Radiology, Nov. 2000, vol. 35 (11), pp. 661-671, Lippincott Williams Wilkinson, Inc., XP009041823.
Grabar, Katherine C. et al., "Preparation and Characterization of Au Colloid Monolayers" Analytical Chemistry, vol. 67, No. 4, Feb. 15, 1995, pp. 735-743.
Kabalka, G.W. et al., "Gadolinium-labeled liposomes containing paramagnetic amphipathic agents: targeted MRI contrast agents for the liver", Magnetic Resonance in Medicine, 1988, pp. 89-95, vol. 8, Academic Press, Inc.
Kim, Tae-Hwan et al: "One more robust estimation of skewness and kurtosis: simulation and application to the S&P500 Index", Department of Economics, USCD, 2003, US.
Malmsten, M., "Surfactants and Polymers in Drug Delivery", 2002, Ch. 2, pp. 19-50, Ch. 4, pp. 87-131, Marcel Dekker Inc. Ed.
Morgan et al: "Experimental and Theoretical Evaluation of Microbubble Behavior: Effect of Transmitted phase and Bubble Size" IEEE Transactions on Ultrasonics, Ferroelectric, and Frequency Control, Nov. 2000, pp. 1494-1509, vol. 47, No. 6.
Patel et al., "Optical and Acoustical Interrogation of Submicron Contrast Agents", IEEE Transactions on Ultrasonics, Ferroelectrics and Frequency Control, 2002, vol. 49, No. 2, pp. 1641-1651.
Scabia et al: "Hardware and software platform for processing and visualization of echographic radio-frequency signals" IEEE Transactions on Ultrasonics, Ferroelectric, and Frequency Control, Oct. 2002, pp. 1444-1452, vol. 49, No. 10.
The Free Dictionary, "microemulsion", http://encyclopedia2.thefreedictionary.com/Microemulsion, 2012.
Office Action for Australian application No. 2005273865, mail date Feb. 5, 2010.
Office Action (First) for Chinese application No. 200580028052.9, mail date May 8, 2009 (English translation).
Office Action (Second) for Chinese application No. 200580028052.9, mail date Mar. 12, 2010 (English translation).
Notification of Re-examination for Chinese application No. 200580028052.9, mail date Mar. 20, 2012 (English translation).
Office Action for Japanese application No. 2007-526459, mail date Feb. 8, 2011 (English translation).
European Search Report for EP04019557.0, mail date Jan. 7, 2005.
PCT International Search Report for PCT/IB2004/004233, mail date May 30, 2005.
PCT Written Opinion for PCT/IB2004/004233, mail date May 30, 2005.
PCT International Preliminary Report on Patentability for PCT/IB2004/004233, mail date Jul. 6, 2006.
PCT International Search Report for PCT/IB2005/004230, mail date May 30, 2005.
PCT Written Opinion for PCT/IB2005/004230, mail date May 30, 2005.
PCT International Search Report for PCT/EP2005/054041, mail date Oct. 28, 2005.
PCT Written Opinion for PCT/EP2005/054041, mail date Oct. 28, 2005.
Uster, et al., "Insertion of poly(ethylene glycol) derivatized phospholipid into pre-formed liposomes results in prolonged in vivo circulation time," FEBS Letters, 386:243-246 (1996).

(56) References Cited

OTHER PUBLICATIONS

Notice of Allowance for U.S. Appl. No. 11/660,188, mail date Dec. 15, 2015.
Notice of Allowance for U.S. Appl. No. 11/660,188, mail date Aug. 25, 2015.
Office Action for U.S. Appl. No. 11/660,188, mail date Dec. 10, 2014.
Office Action for U.S. Appl. No. 11/660,188, mail date Jun. 4, 2014.
Office Action for U.S. Appl. No. 11/660,188, mail date Nov. 15, 2013.
Office Action for U.S. Appl. No. 11/660,188, mail date May 17, 2013.
Office Action for U.S. Appl. No. 11/660,188, mail date Sep. 13, 2012.
Office Action for U.S. Appl. No. 11/660,188, mail date Jul. 7, 2011.
Office Action for U.S. Appl. No. 11/660,188, mail date Dec. 6, 2010.
U.S. Appl. No. 14/981,745, Bussat, Philippe et al., filed Dec. 28, 2015.

* cited by examiner

ULTRASOUND CONTRAST AGENTS AND PROCESS FOR THE PREPARATION THEREOF

This application is the national stage application of corresponding international application number PCT/IB2004/000243 filed Feb. 3, 2004, which claims priority to and the benefit of the European application no. 03002375.8, filed Feb. 4, 2003, all of which are hereby incorporated by reference.

The present invention relates to a process for the preparation of a dry or lyophilized formulation useful for preparing a gas containing contrast agent usable in diagnostic imaging and to a process for preparing said gas containing contrast agent.

The invention also includes dry formulations prepared by this process, which may be reconstituted to form contrast agent suspensions useful in diagnostic imaging. The invention further includes suspensions of gas filled microbubbles useful in diagnostic imaging prepared using dry formulations of the invention as well as containers or two component kits containing the dry formulations of the invention.

BACKGROUND OF THE INVENTION

Rapid development of ultrasound contrast agents in the recent years has generated a number of different formulations, which are useful in ultrasound imaging of organs and tissue of human or animal body. These agents are designed to be used primarily as intravenous or intra-arterial injectables in conjunction with the use of medical echographic equipment which employs for example, B-mode image formation (based on the spatial distribution of backscatter tissue properties) or Doppler signal processing (based on Continuous Wave or pulsed Doppler processing of ultrasonic echoes to determine blood or liquid flow parameters).

A class of injectable formulations useful as ultrasound contrast agents includes suspensions of gas bubbles having a diameter of few microns dispersed in an aqueous medium.

Use of suspensions of gas bubbles in carrier liquid, as efficient ultrasound reflectors is well known in the art. The development of microbubble suspensions as echopharmaceuticals for enhancement of ultrasound imaging followed early observations that rapid intravenous injections of aqueous solutions can cause dissolved gases to come out of solution by forming bubbles. Due to their substantial difference in acoustic impedance relative to blood, these intravascular gas bubbles were found to be excellent reflectors of ultrasound. The injection of suspensions of gas bubbles in a carrier liquid into the blood stream of a living organism strongly reinforces ultrasonic echography imaging, thus enhancing the visualisation of internal organs. Since imaging of organs and deep seated tissues can be crucial in establishing medical diagnosis, a lot of effort has been devoted to the development of stable suspensions of highly concentrated gas bubbles which at the same time would be simple to prepare and administer, would contain a minimum of inactive species and would be capable of long storage and simple distribution.

The simple dispersion of free gas bubbles in the aqueous medium is however of limited practical interest, since these bubbles are in general not stable enough to be useful as ultrasound contrast agents.

Interest has accordingly been shown in methods of stabilising gas bubbles for echography and other ultrasonic studies, for example using emulsifiers, oils, thickeners or sugars, or by entrapping or encapsulating the gas or a precursor thereof in a variety of systems. These stabilized gas bubbles are generally referred to in the art as "microvesicles", and may be divided into two main categories.

A first category of stabilized bubbles or microvesicles is generally referred to in the art as "microbubbles" and includes aqueous suspensions in which the bubbles of gas are bounded at the gas/liquid interface by a very thin envelope involving a surfactant (i.e. an amphiphilic material) disposed at the gas to liquid interface. A second category of microvesicles is generally referred to in the art as "microballoons" or "microcapsules" and includes suspensions in which the bubbles of gas are surrounded by a solid material envelope formed of natural or synthetic polymers. Examples of microballoons and of the preparation thereof are disclosed, for instance, in European patent application EP 0458745. Another kind of ultrasound contrast agent includes suspensions of porous microparticles of polymers or other solids, which carry gas bubbles entrapped within the pores of the microparticles. The present invention is particularly concerned with contrast agents for diagnostic imaging including an aqueous suspension of gas microbubbles, i.e. microvesicles which are stabilized essentially by a layer of amphiphilic material.

Microbubbles suspensions are typically prepared by contacting powdered amphiphilic materials, e.g. freeze-dried preformed liposomes or freeze-dried or spray-dried phospholipid suspensions, with air or other gas and then with aqueous carrier, agitating to generate a microbubble suspension which must then be administered shortly after its preparation.

Examples of aqueous suspensions of gas microbubbles and preparation thereof can be found for instance in U.S. Pat. No. 5,271,928, U.S. Pat. No. 5,445,813, U.S. Pat. No. 5,413,774, U.S. Pat. Nos. 5,556,610, 5,597,549, U.S. Pat. No. 5,827,504.

WO97/29783 discloses an alternative process for preparing gas microbubbles suspensions, comprising generating a gas microbubble dispersion in an appropriate phospholipid-containing aqueous medium and thereafter subjecting the dispersion to lyophilisation to yield a dried reconstitutable product. The so prepared dried products are reconstitutable in aqueous media requiring only minimal agitation. As mentioned in said document, the size of the so generated microbubbles is consistently reproducible and in practice is independent from the amount of agitation energy applied during reconstitution, being determined by the size of the microbubbles formed in the initial microbubble dispersion. The Applicant has however observed that the amount of agitation energy applied for generating the gas microbubble dispersion in the phospholipid-containing aqueous medium may be excessively high, particularly when small diameter microbubbles are to be obtained (e.g. 23000 rpm for 10 minutes, for obtaining a dispersion of bubbles having a volume mean diameter of about 3 µm). This high agitation energy may determine local overheating in the aqueous dispersion of microbubbles, which may in turn cause degradation of the phospholipids contained in the aqueous medium. In addition, the effects of an excessively high agitation energy are in general difficult to control and may result in an uncontrollable size distribution of the final microbubbles. Furthermore, this process involves a continuous flow of gas into the aqueous medium during the generation of microbubbles, thus requiring the use of relevant amounts of gases.

WO 94/01140 discloses a further process for preparing microvesicle suspensions reconstitutable in an aqueous medium, which comprises lyophilizing aqueous emulsions containing parenterally acceptable emulsifiers, non polar liquids and lipid-soluble or water-insoluble "structure-builders". Poloxamers and phospholipids are mentioned as parenterally acceptable emulsifiers, while mixtures of these two are employed in the working examples. Cholesterol is the preferred water-insoluble structure-builder, which is employed in the working examples. The lyophilized product is then reconstituted in water, to give aqueous suspension of gas-filled microvesicles. The gas-filled microvesicles resulting from the reconstitution step are thus defined by an envelope of different materials, including emulsifiers such as poloxamers and water-insoluble structure-builders such as cholesterol.

The process is said to result into an emulsion with particles' size lower than 4 µm, preferably lower than 2 µm, down to 0.5 µm. The Applicant has however noticed that while the reconstitution step may finally result in microvesicles having a numerical mean diameter of less than 2 µm, the corresponding size distribution of the microvesicles population is nevertheless relatively broad. In addition, the conversion step from the emulsion microparticles, obtained according to the above process, into gas microbubbles results in rather low yield.

The Applicant has now found that a much narrower distribution of microbubbles size can be obtained if a phospholipid is used as the main emulsifier of the above emulsion and if the above process is conducted in the substantial absence of the above water-insoluble structure-builders. In addition, the substantial absence of said water-insoluble structure-builders allows to substantially increase the conversion yield from emulsion microparticles into gas microbubbles. The Applicant has further observed that the above process may result in a further narrower size distribution of microbubbles and in an increased yield if the phospholipid is essentially the only emulsifier present in the emulsion.

The Applicant has also found that by applying a rather low agitation energy to an aqueous-organic emulsion during the process as above specified, it is possible to obtain microbubbles having a very small diameter and reduced size distribution.

SUMMARY OF THE INVENTION

An aspect of the present invention relates to a method for preparing a lyophilized matrix which, upon contact with an aqueous carrier liquid and a gas, is reconstitutable into a suspension of gas-filled microbubbles stabilized predominantly by a phospholipid, said method comprising the steps of:
  a) preparing an aqueous-organic emulsion comprising i) an aqueous medium, ii) an organic solvent substantially immiscible with water; iii) an emulsifying composition of amphiphilic materials comprising more than 50% by weight of a phospholipid and iv) a lyoprotecting agent;
  b) lyophilizing said emulsified mixture, to obtain a lyophilized matrix comprising said phospholipid.

Another aspect of the present invention relates to a process for preparing an injectable contrast agent comprising a liquid aqueous suspension of gas-filled microbubbles stabilized predominantly by a phospholipid, which comprises the steps of:
  a) preparing an aqueous-organic emulsion comprising i) an aqueous medium, ii) an organic solvent substantially immiscible with water; iii) an emulsifying composition of amphiphilic materials comprising more than 50% by weight of a phospholipid and iv) a lyoprotecting agent;
  b) lyophilizing said emulsion, to obtain a lyophilized matrix comprising said phospholipid.
  c) contacting said lyophilized matrix with a biocompatible gas;
  d) reconstituting said lyophilized matrix by dissolving it into a physiologically acceptable aqueous carrier liquid, to obtain a suspension of gas-filled microbubbles stabilized predominantly by said phospholipid.

Preferably, the step a) of preparing the emulsion comprises:
  a1) preparing a suspension by dispersing the emulsifying composition of amphiphilic materials and the lyoprotective agent in the aqueous medium;
  a2) admixing the obtained suspension with the organic solvent;
  a3) submitting the mixture to controlled agitation, to obtain an emulsion.

Preferably, the controlled agitation according to step a3) is obtained by using a high pressure homogenizer or more preferably a rotor-stator homogenizer.

A further aspect of the invention relates to an injectable contrast agent comprising a suspension of gas-filled microbubbles stabilized by a stabilizing layer predominantly comprising a phospholipid in an aqueous carrier liquid, wherein said microbubbles have a number mean diameter ($D_N$) of less than 1.70 µm and a volume median diameter ($D_{V50}$) such that the $D_{V50}/D_N$ ratio is of about 2.00 or lower.

DETAILED DESCRIPTION OF THE INVENTION

As mentioned above an aspect of the present invention relates to a method for preparing a lyophilized matrix of a reconstitutable suspension of gas-filled microbubbles predominantly stabilized by a phospholipid, said method comprising the preparation of an aqueous-organic emulsion comprising i) an aqueous medium, ii) an organic solvent substantially immiscible with water; iii) a phospholipid and iv) a lyoprotecting agent, and the subsequent lyophilizing of said emulsion.

The aqueous medium is preferably a physiologically acceptable carrier. The term "physiologically acceptable" includes to any compound, material or formulation which can be administered, in a selected amount, to a patient without negatively affecting or substantially modifying its organism's healthy or normal functioning (e.g. without determining any status of unacceptable toxicity, causing any extreme or uncontrollable allergenic response or determining any abnormal pathological condition or disease status).

Suitable aqueous liquid carriers are water, typically sterile, pyrogen free water (to prevent as much as possible contamination in the intermediate lyophilized product), aqueous solutions such as saline (which may advantageously be balanced so that the final product for injection is not hypotonic), or aqueous solutions of one or more tonicity adjusting substances such as salts or sugars, sugar alcohols, glycols or other non-ionic polyol materials (eg. glucose, sucrose, sorbitol, mannitol, glycerol, polyethylene glycols, propylene glycols and the like).

The Organic Solvent

As used herein the term "substantially immiscible with water" referred to the organic solvent means that, when said solvent is admixed with water, two separate phases are formed. Water immiscible solvent are generally also known in the art as apolar or non-polar solvents, as opposed to polar solvents (such as water). Water immiscible solvents are in general substantially insoluble in water. For the purposes of the present invention, organic solvents suitable for being emulsified with the aqueous solvent are typically those solvents having a solubility in water of less than about 10 g/l. Preferably, the solubility of said solvent in water is of about 1.0 g/l or lower, more preferably about 0.2 g/l or lower and much more preferably about 0.01 g/l or lower. Particularly preferred solvents are those having a solubility in water of 0.001 g/l or lower. Particularly insoluble organic solvents (e.g. perfluorocarbons) may have a solubility down to about $1.0 \cdot 10^{-6}$ g/l (e.g perfluorooctane, $1.66 \cdot 10^{-6}$ g/l).

The organic solvent is preferably lyophilisable, i.e. said solvent has a sufficiently high vapour pressure at the lyophilization temperatures, e.g. between −30° C. and 0° C., to allow for an effective and complete evaporation/sublimation within acceptable times, e.g. 24-48 hours. Preferably, the vapour pressure of the organic solvent is higher than about 0.2 kPa at 25° C.

The organic solvent can be selected from a broad range of solvents and any chemical entity that is water-immiscible and lyophilisable, as indicated above, and being preferably liquid at room temperature (25° C.). If a solvent having a boiling point lower than room temperature is used, the vessel containing the emulsifying mixture can advantageously be cooled below the boiling point of said solvent, e.g. down to 5° C. or 0° C. As said solvent will be completely removed during the lyophilization step, no particular constraints exist except that it should not contain contaminants that cannot be removed through lyophilisation or that are not acceptable for use in an injectable composition. Suitable organic solvents include but are not limited to alkanes, such as branched or, preferably, linear ($C_5$-$C_{10}$) alkanes, e.g. pentane, hexane, heptane, octane, nonane, decane; alkenes, such as ($C_5$-$C_{10}$) alkenes, e.g. 1-pentene, 2-pentene, 1-octene; cyclo-alkanes, such as ($C_5$-$C_8$)-cycloalkanes optionally substituted with one or two methyl groups, e.g. cyclopentane, cyclohexane, cyclooctane, 1-methyl-cyclohexane; aromatic hydrocarbons, such as benzene and benzene derivatives substituted by one or two methyl or ethyl groups, e.g. benzene, toluene, ethylbenzene, 1,2-dimethylbenzene, 1,3-dimethylbenzene; alkyl ethers and ketones such as di-butyl ether and di-isopropylketone; halogenated hydrocarbons or ethers, such as chloroform, carbon tetrachloride, 2-chloro-1-(difluoromethoxy)-1,1,2-trifluoroethane (enflurane), 2-chloro-2-(difluoromethoxy)-1,1,1-trifluoroethane (isoflurane), tetrachloro-1,1-difluoroethane, and particularly perfluorinated hydrocarbons or ethers, such as perfluoropentane, perfluorohexane, perfluoroheptane, perfluoromethylcyclohexane, perfluorooctane, perfluorononane, perfluorobenzene and perfluorodecalin, methylperfluorobutylether, methylperfluoroisobutylether, ethylperfluorobutylether, ethylperfluoroisobutylether; and mixtures thereof.

The amount of solvent is generally comprised from about 1% to about 50% by volume with respect to the amount of water used for the emulsion. Preferably said amount is from about 1% to about 20%, more preferably from about 2% to about 15% and even more preferably from about 5% to about 10%. If desired, a mixture of two or more of the above listed organic solvents can be used, the overall amount of organic solvent in the emulsifying mixture being within the above range.

Lyoprotective Agent

The term lyoprotective agent or "lyoprotectant" refers to a compound which, when included in a formulation to be lyophilized, will protect the chemical compounds from the deleterious effects of freezing and vacuumizing, such as those usually accompanying lyophilization, e.g. damage, adsorption and loss from vacuum utilized in lyophilization. In addition, after the lyophilization step, said lyoprotective agent preferably results in a solid matrix ("bulk") which supports the lyophilized phospholipid.

The present invention is not limited to the use of a specific lyoprotectant, and examples of suitable lyoprotectants include, but are not limited to, carbohydrates such as the saccharides, mono-, di- or poly-saccharides, e.g. glucose, galactose, fructose, sucrose, trehalose, maltose, lactose, amylose, amylopectin, cyclodextrins, dextran, inuline, soluble starch, hydroxyethyl starch (HES), sugar alcohols e.g. mannitol, sorbitol and polyglycols such as polyethyleneglycols. A substantial list of agents with lyoprotective effects is given in Acta Pharm. Technol. 34(3), pp. 129-139 (1988), the content of which is incorporated herein by reference. Said lyoprotective agents can be used singularly or as mixtures of one or more compounds.

Preferred lyoprotectants include mannitol and polysaccharides such as dextrans (in particular those with molecular weights above 1500 daltons), inulin, soluble starch, and hydroxyethyl starch.

Mixtures of mannitol or polysaccharides such as dextrans, inulin, soluble starch, hydroxyethyl starch with saccharides such as glucose, maltose, lactose, sucrose, trehalose and erythritol also provide excellent results.

Likewise, the present invention is not limited to any particular amount of lyoprotectant used. However the optimal weight concentration of lyoprotective agents in the emulsion prior to the lyophilisation is comprised between about 1 and about 25%, preferably between about 2 and about 20%, and even more preferably between about 5 and about 10%.

A higher amount can be employed if it is also necessary to provide a desired "bulk" to the lyophilized product.

The lyoprotective agent is preferably added to the aqueous-organic mixture before emulsification of the same and in this case the emulsification of the aqueous-organic mixture is thus carried out in the presence of the lyoprotective agents. Alternatively, the lyoprotectant can be added to the aqueous-organic mixture after the emulsification thereof. In the first case, the lyoprotectant is preferably added to the aqueous medium, before admixing it with the organic solvent. If desired, it is also possible to combine the two, e.g. by adding part of the lyoprotective agent to the aqueous phase used for the preparation of the emulsion and part to the thus obtained emulsion. If desired, also cryoprotective agents, such as glycerol, can further be added to the emulsion for protecting the chemical compounds from the deleterious effects of freezing.

Phospholipids

According to the present description and claims, the term phospholipid is intended to encompass any amphiphilic phospholipidic compound the molecules of which are capable of forming a film of material (typically in the form of a monomolecular layer) at the gas-water boundary interface in the final microbubbles suspension. Accordingly, these material are also referred to in the art as "film-forming phospholipids". Similarly, in the emulsified mixture, these amphiphilic compounds are typically disposed at the interface between the aqueous medium and the organic solvent substantially insoluble in water, thus stabilizing the emulsified solvent microdroplets. The film formed by these compounds at the gas-water or water-solvent interface can be either continuous or discontinuous. In the latter case, the discontinuities in the film should not however be such as to impair the stability (e.g. pressure resistance, resistance to coalescence, etc.) of the suspended microbubbles or of the emulsified microdroplets, respectively.

The term "amphiphilic compound" as used herein includes compounds having a molecule with a hydrophilic polar head portion (e.g. a polar or ionic group), capable of interacting with an aqueous medium, and a hydrophobic organic tail portion (e.g. a hydrocarbon chain), capable of interacting with e.g. an organic solvent. These compounds thus generally act as "surface active agent", i.e. compounds which are capable of stabilizing mixtures of otherwise generally immiscible materials, such as mixtures of two immiscible liquids (e.g. water and oil), mixtures of liquids with gases (e.g. gas microbubbles in water) or mixtures of liquids with insoluble particles (e.g. metal nanoparticles in water).

Amphiphilic phospholipid compounds typically contain at least one phosphate group and at least one, preferably two, lipophilic long-chain hydrocarbon group.

Examples of suitable phospholipids include esters of glycerol with one or preferably two (equal or different) residues of fatty acids and with phosphoric acid, wherein the phosphoric acid residue is in turn bound to a hydrophilic group, such as choline (phosphatidylcholines—PC), serine (phosphatidylserines—PS), glycerol (phosphatidylglycerols—PG), ethanolamine (phosphatidylethanolamines—PE), inositol (phosphatidylinositol), and the like groups. Esters of phospholipids with only one residue of fatty acid are generally referred to in the art as the "lyso" forms of the phospholipid. Fatty acids residues present in the phospholipids are in general long chain aliphatic acids, typically containing from 12 to 24 carbon atoms, preferably from 14 to 22; the aliphatic chain may contain one or more unsaturations or is preferably completely saturated. Examples of suitable fatty acids included in the phospholipids are, for instance, lauric acid, myristic acid, palmitic acid, stearic acid, arachidic acid, behenic acid, oleic acid, linoleic acid, and linolenic acid. Preferably, saturated fatty acids such as myristic acid, palmitic acid, stearic acid and arachidic acid are employed.

Further examples of phospholipid are phosphatidic acids, i.e. the diesters of glycerol-phosphoric acid with fatty acids; sphingolipids such as sphingomyelins, i.e. those phosphatidylcholine analogs where the residue of glycerol diester with fatty acids is replaced by a ceramide chain; cardiolipins, i.e. the esters of 1,3-diphosphatidylglycerol with a fatty acid; glycolipids such as gangliosides GM1 (or GM2) or cerebrosides; glucolipids; sulfatides and glycosphingolipids.

As used herein, the term phospholipids include either naturally occurring, semisynthetic or synthetically prepared products that can be employed either singularly or as mixtures.

Examples of naturally occurring phospholipids are natural lecithins (phosphatidylcholine (PC) derivatives) such as, typically, soya bean or egg yolk lecithins.

Examples of semisynthetic phospholipids are the partially or fully hydrogenated derivatives of the naturally occurring lecithins. Preferred phospholipids are fatty acids di-esters of phosphatidylcholine, ethylphosphatidylcholine, phosphatidylglycerol, phosphatidic acid, phosphatidylethanolamine, phosphatidylserine or of sphingomyelin.

Examples of preferred phospholipids are, for instance, dilauroyl-phosphatidylcholine (DLPC), dimyristoyl-phosphatidylcholine (DMPC), dipalmitoyl-phosphatidylcholine (DPPC), diarachidoyl-phosphatidylcholine (DAPC), distearoyl-phosphatidylcholine (DSPC), dioleoyl-phosphatidylcholine (DOPC), 1,2 Distearoyl-sn-glycero-3-Ethylphosphocholine (Ethyl-DSPC), dipentadecanoyl-phosphatidylcholine (DPDPC), 1-myristoyl-2-palmitoyl-phosphatidylcholine (MPPC), 1-palmitoyl-2-myristoyl-phosphatidylcholine (PMPC), 1-palmitoyl-2-stearoyl-phosphatidylcholine (PSPC), 1-stearoyl-2-palmitoyl-phosphatidylcholine (SPPC,), 1-palmitoyl-2-oleylphosphatidylcholine (POPC), 1-oleyl-2-palmitoyl-phosphatidylcholine (OPPC), dilauroyl-phosphatidylglycerol (DLPG) and its alkali metal salts, diarachidoylphosphatidyl-glycerol (DAPG) and its alkali metal salts, dimyristoylphosphatidylglycerol (DMPG) and its alkali metal salts, dipalmitoylphosphatidylglycerol (DPPG) and its alkali metal salts, distearoylphosphatidylglycerol (DSPG) and its alkali metal salts, dioleoyl-phosphatidylglycerol (DOPG) and its alkali metal salts, dimyristoyl phosphatidic acid (DMPA) and its alkali metal salts, dipalmitoyl phosphatidic acid (DPPA) and its alkali metal salts, distearoyl phosphatidic acid (DSPA), diarachidoylphosphatidic acid (DAPA) and its alkali metal salts, dimyristoyl-phosphatidylethanolamine (DMPE), dipalmitoylphosphatidylethanolamine (DPPE), distearoyl phosphatidyl-ethanolamine (DSPE), dioleylphosphatidylethanolamine (DOPE), diarachidoylphosphatidylethanolamine (DAPE), dilinoleylphosphatidylethanolamine (DLPE), dimyristoyl phosphatidylserine (DMPS), diarachidoyl phosphatidylserine (DAPS), dipalmitoyl phosphatidylserine (DPPS), distearoylphosphatidylserine (DSPS), dioleoylphosphatidylserine (DOPS), dipalmitoyl sphingomyelin (DPSP), and distearoylsphingomyelin (DSSP).

The term phospholipid further includes modified phospholipid, e.g. phospholipids where the hydrophilic group is in turn bound to another hydrophilic group. Examples of modified phospholipids are phosphatidylethanolamines modified with polyethylenglycol (PEG), i.e. phosphatidylethanolamines where the hydrophilic ethanolamine moiety is linked to a PEG molecule of variable molecular weight e.g. from 300 to 5000 daltons, such as DPPE-PEG or DSPE-PEG, i.e. DPPE (or DSPE) having a PEG polymer attached thereto. For example, DPPE-PEG2000 refers to DPPE having attached thereto a PEG polymer having a mean average molecular weight of about 2000. As explained in detail in the following, these PEG-modified phospholipids are preferably used in combination with non-modified phospholipids.

Both neutral and charged phospholipids can satisfactorily be employed in the process of the present invention, as well as mixtures thereof. As used herein and in the prior art, the term "charged" in relation with "phospholipids" means that the individual phospholipid molecules have an overall net charge, be it positive or, more frequently, negative.

Examples of phospholipids bearing an overall negative charge are derivatives, in particular fatty acid di-esters, of phosphatidylserine, such as DMPS, DPPS, DSPS; of phosphatidic acid, such as DMPA, DPPA, DSPA; of phosphatidylglycerol such as DMPG, DPPG and DSPG. Also modified phospholipids, in particular PEG-modified phosphatidylethanolamines, such as DMPE-PEG750, DMPE-PEG1000, DMPE-PEG2000, DMPE-PEG3000, DMPE-PEG4000, DMPE-PEG5000, DPPE-PEG750, DPPE-PEG1000, DPPE-PEG2000, DPPE-PEG3000, DPPE-PEG4000, DPPE-PEG5000, DSPE-PEG750, DSPE-PEG1000, DSPE-PEG2000, DSPE-PEG3000, DSPE-PEG4000, DSPE-PEG5000, DAPE-PEG750, DAPE-PEG1000, DAPE-PEG2000, DAPE-PEG3000, DAPE-PEG4000 or DAPE-PEG5000 can be used as negatively charged molecules. Also the lyso-form of the above cited phospholipids, such as lyso-phosphatidylserine derivatives (e.g. lyso-DMPS, -DPPS or -DSPS), lysophosphatidic acid derivatives (e.g. lyso-DMPA, -DPPA or -DSPA) and lysophosphatidylglycerol derivatives (e.g. lyso-DMPG, -DPPG or -DSPG), can advantageously be used as negatively charged compound.

Examples of phospholipids bearing an overall positive charge are derivatives of ethylphosphatidylcholine, in particular esters of ethylphosphatidylcholine with fatty acids, such as 1,2-Distearoyl-sn-glycero-3-Ethylphosphocholine (Ethyl-DSPC or DSEPC), 1,2-Dipalmitoyl-sn-glycero-3-Ethylphosphocholine (Ethyl-DPPC or DPEPC).

Preferably, blends of two or more phospholipids, at least one with a neutral charge and at least one with an overall net charge, are employed. More preferably, blends of two or more phospholipids, at least one with neutral and at least one with negative charge are employed. The amount of charged phospholipid, may vary from about 95% to about 5% by weight, with respect to the total amount of phospholipid, preferably from 80% to 20% by weight. The presence of at least minor amounts, such as 5% to 20% by wt. with respect to the total weight of phospholipid, of a (negatively) charged phospholipid may help preventing aggregation of bubbles or emulsion droplets. It is however possible to use a single phospholipid, neutral or charged, or a blend of two or more phospholipids, all neutral or all with an overall net charge.

Preferred phospholipids are DAPC, DPPA, DSPA, DMPS, DPPS, DSPS, DPPE, DSPE, DSPG, DPPG and Ethyl-DSPC. Most preferred are DSPA, DPPS or DSPS.

Preferred mixtures of phospholipids are mixtures of DPPS with DPPC, DSPC or DAPC (from 95/5 to 5/95 w/w), mixtures of DSPA with DSPC or DAPC (from 95/5 to 5/95 w/w), mixtures or DSPG or DPPG with DSPC or mixtures of DSPC with Ethyl-DSPC. Most preferred are mixtures of DPPS/DSPC (from 50/50 to 10/90 w/w) or DSPA/DSPC (from 50/50 to 20/80 w/w).

The amount of phospholipid is generally comprised between about 0.005 and about 1.0% by weight with respect to the total weight of the emulsified mixture. Larger amounts might of course be employed but considering that the end product is an injectable contrast agent, it is preferred not to use excess of additives unless strictly necessary to provide for a stable and suitable product. In general, by using an amount of phospholipid larger than that indicated as the upper limit of the above range, essentially no or a very negligible improvement is observed in terms of bubble population, bubble size distribution, and bubble stability. Typically, higher amounts of phospholipid are required when higher volumes of organic solvent are used. Thus, when the volume of organic solvent amounts to about 50% the volume of the water phase, an amount of about 1% w/w of phospholipid can advantageously be added to the emulsion. Preferably the amount of phospholipid is comprised between 0.01 and 1.0% by weight with respect to the total weight of the emulsified mixture and more preferably between about 0.05% and 0.5% by weight.

As mentioned before, the microbubbles produced according to the process of the invention are stabilized predominantly by a phospholipid, as above defined. In particular, the envelope surrounding the gas filled microbubbles is formed by more than 50% (w/w), preferably by at least 80%, and much more preferably by at least 90% of a phospholipid material as above defined. Conveniently, the substantial totality of the stabilizing envelope of the microbubbles is formed by a phospholipid.

Other amphiphilic materials can however be admixed with the phospholipids forming the stabilizing envelope of the gas-filled microbubbles, in amounts of less than 50% of the total weight of the emulsifying composition.

Examples of suitable additional envelope-stabilizing amphiphilic materials include, for instance, lysolipids; fatty acids, such as palmitic acid, stearic acid, lauric acid, myristic acid, arachidic acid, arachidonic acid, behenic acid, oleic acid, linoleic acid or linolenic acid, and their respective salts with alkali or alkali metals; lipids bearing polymers, such as chitin, hyaluronic acid, polyvinylpyrrolidone or polyethylene glycol (PEG), also referred as "pegylated lipids"; lipids bearing sulfonated mono- di-, oligo- or polysaccharides; lipids with ether or ester-linked fatty acids; polymerized lipids; diacetyl phosphate; dicetyl phosphate; stearylamine; ceramides; polyoxyethylene fatty acid esters (such as polyoxyethylene fatty acid stearates); polyoxyethylene fatty alcohols; polyoxyethylene fatty alcohol ethers; polyoxyethylated sorbitan fatty acid esters; glycerol polyethylene glycol ricinoleate; ethoxylated soybean sterols; ethoxylated castor oil; ethylene oxide (EO) and propylene oxide (PO) block copolymers; sterol esters of sugar acids including cholesterol glucuronides, lanosterol glucoronides, 7-dehydrocholesterol glucoronide, ergosterol glucoronide, cholesterol gluconate, lanosterol gluconate, or ergosterol gluconate; esters of sugar acids and alcohols including lauryl glucoronide, stearoyl glucoronide, myristoyl glucoronide, lauryl gluconate, myristoyl gluconate, or stearoyl gluconate; esters of sugars with aliphatic acids including sucrose laurate, fructose laurate, sucrose palmitate, sucrose stearate, glucuronic acid, gluconic acid or polyuronic acid; esters of glycerol with ($C_{12}$-$C_{24}$), preferably ($C_{14}$-$C_{22}$) dicarboxylic fatty acids and their respective salts with alkali or alkali-metal salts, such as 1,2-dipalmitoyl-sn-3-succinylglycerol or 1,3-dipalmitoyl-2-succinylglycerol; saponins including sarsasapogenin, smilagenin, hederagenin, oleanolic acid, or digitoxigenin; long chain ($C_{12}$-$C_{24}$) alcohols, including n-decyl alcohol, lauryl alcohol, myristyl alcohol, cetyl alcohol, or n-octadecyl alcohol; 6-(5-cholesten-3β-yloxy)-1-thio-β-D-galactopyranoside; digalactosyldiglyceride; 6-(5-cholesten-3β-yloxy)hexyl-6-amino-6-deoxy-1-thio-β-D-galactopyranoside; 6-(5-cholesten-3β-yloxy)hexyl-6-amino-6-deoxyl-1-thio-β-D-mannopyranoside; 12-(((7'-diethylaminocoumarin-3-yl)carbonyl)methylamino)octadecanoic acid; N-[12-(((7'-diethylaminocoumarin-3-yl)carbonyl)methylamino)octadecanoyl]-2-aminopalmitic acid; N-succinyldioleylphosphatidylethanolamine; 1-hexadecyl-2-palmitoylglycerophosphoethanolamine; palmitoylhomocysteine; alkylammonium salts comprising at least one ($C_{10}$-$C_{20}$), preferably ($C_{14}$-$C_{18}$), alkyl chain, such as, for instance, stearylammonium chloride, hexadecylammonium chloride, dimethyldioctadecylammonium bromide (DDAB), hexadecyltrimethylammonium bromide (CTAB); tertiary or quaternary ammonium salts comprising one or preferably two ($C_{10}$-$C_{20}$), preferably ($C_{14}$-$C_{18}$), acyl ester residue, such as, for instance, 1,2-distearoyl-3-trimethylammonium-propane (DSTAP), 1,2-dipalmitoyl-3-trimethylammonium-propane (DPTAP), 1,2-oleoyl-3-trimethylammonium-propane (DOTAP), 1,2-distearoyl-3-dimethylammonium-propane (DSDAP): and mixtures or combinations thereof.

Small amounts of fatty acids and lyso forms of the phospholipids may also form as degradation products of the original phospholipid products, e.g. as a consequence of heating the emulsion.

Preferred additional envelope-stabilizing amphiphilic materials are those compounds comprising one or two fatty acid residues in their molecule, in particular one or two linear ($C_{10}$-$C_{20}$)-acyl, preferably ($C_{14}$-$C_{18}$)-acyl chains, such as, for instance, the above listed fatty acids, their respective salts and derivatives.

Particularly preferred additional envelope-stabilizing amphiphilic materials are those compounds capable of conferring an overall net charge to the stabilizing envelope, i.e. compounds bearing an overall positive or negative net charge. Examples of suitable negatively of positively charged compounds are, for instance, lyso-phospholipids, i.e. the lyso-form of the above cited phospholipids, such as lysophosphatidylserine derivatives (e.g. lyso-DMPS, -DPPS or -DSPS), lysophosphatidic acid derivatives (e.g. lyso-DMPA, -DPPA or -DSPA) and lysophosphatidylglycerol derivatives (e.g. lyso-DMPG, -DPPG or -DSPG); bile acid salts such as cholic acid salts, deoxycholic acid salts or glycocholic acid salts; ($C_{12}$-$C_{24}$), preferably ($C_{14}$-$C_{22}$) fatty acid salts such as, for instance, palmitic acid salt, stearic acid salt, 1,2-dipalmitoyl-sn-3-succinylglycerol salt or 1,3-dipalmitoyl-2-succinylglycerol salt; alkylammonium salts with a halogen counter ion (e.g. chlorine or bromine) comprising at least one ($C_{10}$-$C_{20}$) alkyl chain, preferably ($C_{14}$-$C_{18}$) alkyl chain, such as, for instance stearylammonium chloride, hexadecylammonium chloride, dimethyldioctadecylammonium bromide (DDAB), hexadecyltrimethylammonium bromide (CTAB); tertiary or quaternary ammonium salts with a halogen counter ion (e.g. chlorine or bromine) comprising one or preferably two ($C_{10}$-$C_{20}$) acyl chain, preferably ($C_{14}$-$C_{18}$) acyl ester residue, such as, for instance, 1,2-distearoyl-3-trimethylammonium-propane (DSTAP), 1,2-dipalmitoyl-3-trimethylammonium-propane (DPTAP), 1,2-oleoyl-3-trimethylammonium-propane (DOTAP), 1,2-distearoyl-3-dimethylammonium-propane (DSDAP).

If it is desired to obtain "targeted" ultrasound contrast agents, i.e. contrast agents containing microbubbles that could selectively bind to a specific site after in vitro or in vivo administration, according to the process of the present invention it is also possible to start directly from a phospholipid at least part of which has been modified by the introduction of a suitably selected targeting ligand or alternatively, and preferably, starting from phospholipid at least part of which contain a possibly protected reactive group capable of being coupled at a later stage with the suitably selected targeting ligand containing a complementary reactive function (e.g. avidin-biotin link).

Therefore, in this specific context, the term "phospholipid" is intended to encompass both modified and unmodified phospholipids, thus including phospholipids modified by linking a targeting ligand or a protective reactive group to the amphiphilic molecule of the phospholipid.

The term "targeting ligand" includes within its meaning any compound, moiety or residue having, or being capable to promote, a targeting activity of the microbubbles of the invention towards any biological or pathological site within a living body. Materials or substances which may serve as targeting ligands include, for example, but are not limited to proteins, including antibodies, antibody fragments, receptor molecules, receptor binding molecules, glycoproteins and lectins; peptides, including oligopeptides and polypeptides; peptidomimetics; saccharides, including mono and polysaccharides; vitamins; steroids, steroid analogs, hormones, cofactors, bioactive agents and genetic material, including nucleosides, nucleotides and polynucleotides. Targets to which targeting ligand may be associated include tissues such as, for instance, myocardial tissue (including myocardial cells and cardiomyocites), membranous tissues (including endothelium and epithelium), laminae, connective tissue (including interstitial tissue) or tumors; blood clots; and receptors such as, for instance, cell-surface receptors for peptide hormones, neurotransmitters, antigens, complement fragments, and immunoglobulins and cytoplasmic receptors for steroid hormones.

Examples of suitable targets and targeting ligands are disclosed, for instance, in U.S. Pat. No. 6,139,819, which is herein incorporated by reference.

In one preferred embodiment the targeting ligands can be bound to the amphiphilic molecules forming the stabilizing envelope through a covalent bond.

In such a case the specific reactive moiety that needs to be present in the phospholipid or lipid molecule when a targeting amphiphilic molecule is desired, will depend on the particular targeting ligand to be coupled thereto. As an example, if the targeting ligand can be linked to the amphiphilic molecule through an amino group, suitable reactive moieties for the amphiphilic molecule may be isothiocyanate groups (that will form a thiourea bond), reactive esters (to form an amide bond), aldehyde groups (for the formation of an imine bond to be reduced to an alkylamine bond), etc.; if the targeting ligand can be linked to the amphiphilic molecule through a thiol group, suitable complementary reactive moieties for the amphiphilic molecule include haloacetyl derivatives or maleimides (to form a thioether bond); and if the targeting ligand can be linked to the amphiphilic molecule through a carboxylic group, suitable reactive moieties for the amphiphilic molecule might be amines and hydrazides (to form amide or alkylamide bonds). The reactive moiety can be linked either directly to the phospholipid molecule or to a modifying moiety (e.g. PEG) linked to the phospholipid.

As indicated above, in a preferred embodiment, when a contrast agent containing targeted microbubbles is desired, at least part of the starting phospholipid will contain a suitable reactive moiety and the targeting ligand containing the complementary functionality will be linked thereto either at any step before the lyophilization, by adding the targeting ligand containing the complementary functionality into the phase containing the functionalised phospholipids/lipids, either before, during or after the generation of the emulsion, or just before the reconstitution step. In this latter case it would be possible to fully exploit the flexibility of the system as the microbubbles containing at least part of the film-forming phospholipids, or of the associated lipids, suitably functionalised, might then be bound to any desired targeting ligand, sharing the same reactive complementary group.

Not necessarily however the targeting ligand needs to be bound to the amphiphilic molecules through a covalent bond. The targeting ligands may also be suitably associated to the microbubbles via physical and/or electrostatic types of interactions. As an example, a functional moiety having a high affinity and selectivity for a complementary moiety can be introduced into the phospholipid molecule, while the complementary moiety will be linked to the targeting ligand. For instance, an avidin (or streptavidin) moiety (having high affinity for biotin) can be covalently linked to a microbubble stabilizing phospholipid while the complementary biotin moiety can be incorporated into a suitable targeting ligand, e.g. a peptide or an antibody. The biotin-labelled targeting ligand will thus be associated to the avidin-labelled microbubble by means of the avidin-biotin coupling system. According to an alternative embodiment, a biotin-containing phospholipid can be used as a compound to form the stabilizing envelope of a microbubble; biotin-containing phospholipid incorporated in the stabilizing envelope is then reacted first with avidin (or neutravidin) and then with a biotin-containing ligand. Examples of biotin/avidin labelling of phospholipids and peptides are also disclosed in the above cited U.S. Pat. No. 6,139,819. Alternatively, van der Waal's interactions, electrostatic interactions and other association processes may associate or bind the targeting ligand to the amphiphilic molecules.

Examples of suitable specific targets to which the microbubbles of the Invention can be directed are, for instance, fibrin, the $\alpha_v\beta_3$ receptor or the GPIIbIIIa receptor on activated platelets. Fibrin and platelets are in fact generally present in "thrombi", i.e. coagula which may form in the blood stream and cause a vascular obstruction. Suitable binding peptides are disclosed, for instance, in the above cited U.S. Pat. No. 6,139,819. Further binding peptides specific for fibrin-targeting are disclosed, for instance, in International patent application WO 02/055544, which is herein incorporated by reference.

Other examples of important targets include receptors in vulnerable plaques and tumor specific receptors, such as kinase domain region (KDR) and VEGF (vascular endothelial growth factor)/KDR complex. Binding peptides suitable for KDR or VEGF/KDR complex are disclosed, for instance, in International Patent application WO 03/74005 and WO 03/084574, both herein incorporated by reference.

Process

The emulsifying step a) of the process of the present invention can be carried out by submitting the aqueous medium and the core solvent in the presence of at least one phospholipid to any appropriate emulsion-generating technique known in the art, such as, for instance, sonication, shaking, high pressure homogenization, micromixing, membrane emulsification, high speed stirring or high shear mixing, e.g. using a rotor-stator homogenizer. For instance, a rotor-stator homogenizer is employed, such as Polytron® PT3000. The agitation speed of the rotor-stator homogenizer can be selected depending from the components of the emulsion, the volume of the emulsion and of the diameter of the vessel containing the emulsion and the desired final diameter of the microdroplets of solvent in the emulsion. In general, it has been observed that, when using a rotor-stator homogenizer having a probe of about 3 cm diameter immersed in a 50-80 ml mixture contained in 3.5-5 cm diameter beaker, an agitation speed of about 8000 rpm is typically sufficient to obtain microdroplets having a mean numerical diameter sufficiently reduced to result, after lyophilization and reconstitution of the lyophilized matrix, in gas-filled microbubbles having a diameter of less than about 1.8 µm. By increasing the agitation speed at about 12000 rpm, it is in general possible to obtain gas-filled microbubbles having a number mean diameter of less than about 1.5 µm, while with an agitation speed of about 14000-15000 rpm, gas-filled microbubbles having a number mean diameter of about 1.0 µm or less can generally be obtained. In general it has been observed that by increasing the agitation speed above about 18000 rpm, slight further reduction of microbubbles size is obtained.

Alternatively, a micromixing technique can also be employed for emulsifying the mixture. As known, a micromixer typically contain at least two inlets and at least one outlet. The organic solvent is thus introduced into the mixer through a first inlet (at a flow rate of e.g. 0.05-5 ml/min), while the aqueous phase is introduced through the second inlet (e.g. at a flow rate of 2-100 ml/min). The outlet of the micromixer is then connected to the vessel containing the aqueous, so that the aqueous phase drawn from said vessel at subsequent instants and introduced into the micromixer contains increasing amounts of emulsified solvent. When the whole volume of solvent has been added, the emulsion from the container can be kept under recirculation through the micromixer for a further predetermined period of time, e.g. 5-120 minutes, to allow completion of the emulsion.

Depending on the emulsion technique, the organic solvent can be introduced gradually during the emulsification step or at once before starting the emulsification step. Alternatively the aqueous medium may be gradually added to the water immiscible solvent during the emulsification step or at once before starting the emulsification step. Preferably, the phospholipid is dispersed in the aqueous medium before this latter is admixed with the organic solvent. Alternatively, the phospholipid can be dispersed in the organic solvent or it may be separately added the aqueous-organic mixture before or during the emulsification step.

The emulsification of step a) is conveniently carried out at room temperature, e.g. at a temperature of 22° C.±5° C., or at higher temperatures, for instance 50° C.-60° C. (e.g. In the case of core solvents with high boiling points) or at lower temperature, for instance 0° C.-10° C. (e.g. in the case of core solvents with boiling points close to room temperature). The temperature is preferably kept below the boiling temperature of the organic solvent, preferably at least 5° C. below said temperature, more preferably at least 10° C. below. As prolonged exposure of the mixture at high temperatures (e.g. 90° C. or more) may cause possible degradations of phospholipids, with consequent formation of of the respective lyso-derivatives, it is in general preferred to avoid such prolonged heating at high temperatures.

If necessary, the aqueous medium containing the phospholipids can be subjected to controlled heating, in order to facilitate the dispersion thereof. For instance, the phospholipid containing aqueous suspension can be heated at about 60-70° C. for about 15 minutes and then allowed to cool at the temperature at which the emulsion step is then carried out.

As previously mentioned, additional amphiphilic materials, such as those previously listed, can also be introduced into the emulsifying mixture containing the phospholipid. The amount of said additional amphiphilic compounds is preferably not higher than about 50% by weight with respect to the total weight of amphiphilic material, more preferably not higher than 20% by weight, down to an amount of e.g. about 0.1%.

The aqueous medium may, if desired, further contain one or more excipients.

As used herein, the term "excipient" refers to any additive useful in the present invention, such as those additives employed to increase the stability of the emulsion or of the lyophilisate intermediate and/or to provide for pharmaceutically acceptable and stable final compositions.

Exemplary excipients in this regard are, for instance, viscosity enhancers and/or solubility aids for the phospholipids.

Viscosity enhancers and solubility aids that may suitably be employed are for example mono- or polysaccharides, such as glucose, lactose, saccharose, and dextrans, aliphatic alcohols, such as isopropyl alcohol and butyl alcohol, polyols such as glycerol, 1,2-propanediol, and the like agents. In general however we have found that it is unnecessary to incorporate additives such as viscosity enhancers, which are commonly employed in many existing contrast agent formulations, into the contrast agents of the present invention. This is a further advantage of the present invention as the number of components administered to the body of a subject is kept to a minimum and the viscosity of the contrast agents is maintained as low as possible.

As mentioned before, the Applicant has found substantially unnecessary, to add water-insoluble structure-builders, such as cholesterol, to the emulsifying mixture. As a matter of fact, it has been observed that an amount of 0.05% (w/w with respect to the total weight of the emulsifying mixture) of cholesterol dramatically reduces the conversion yield from microdroplets into gas-filled microvesicles, further resulting in a broad-dispersion of the vesicles' size. The amount of water-insoluble compounds in the emulsifying mixture, particularly of those compounds not comprising one or two fatty acid residue in their structure, is thus preferably lower than 0.050%, more preferably lower than about 0.030% by weight with respect to the total weight of the emulsion.

Emulsions produced according to step a) may advantageously be subjected to one or more washing steps, prior to the lyophilization of step b), in order to remove excess of phospholipids in the aqueous phase (not associated to the emulsion) and separate and remove optional additives such as viscosity enhancers and solubility aids, as well as undesired material such as colloidal particles, and undersized and/or oversized emulsion droplets. Such washing may be effected in per se known manner, the emulsion being separated using techniques such as decantation, flotation, centrifugation, cross flow filtration and the like.

If washing steps are foreseen, and if a lyoprotective agent was present in the original aqueous phase prior to the generation of the emulsion, said washing steps can be performed with aqueous solutions containing one or more lyoprotective agents to replace the amount of lyoprotective agents partially removed with the washings. On the other side, if no lyoprotectant was present in the emulsified aqueous-organic mixture, the formed emulsion can be washed with a lyoprotectant-containing aqueous solution, in order to introduce the lyoprotectant into the emulsified mixture or, alternatively, the lyoprotectant can be added after the washing steps, prior to lyophilisation.

If desired, the emulsion (either as such or after the washing step) can be subjected to a ultrafiltration or microfiltration step before lyophilization, in order to further reduce the amount of large size microbubbles in the final reconstituted suspension. During microfiltration, e.g. with a 5 µm or 3 µm filter, large size microdroplets are in fact retained by the filter and separated from the rest of the small size microdroplets, thus preventing the formation of large size microbubbles upon reconstitution of the lyophilized material. Microfiltration can be accomplished according to conventional techniques such as positive filtration, vacuum filtration or in-line filtration. Membranes of filtration can be Nylon, glass fiber, cellulose, paper, polycarbonate or polyester (Nuclepore®) membranes.

According to an alternative embodiment, an additional amphiphilic compound can be added after the formation of the emulsion according to the above teachings, either with or without the washing steps. In particular, an aqueous suspension of the desired compound is added to the formed emulsion, preferably under agitation and heating (preferably at less than 80° C., e.g. 40° C.-80° C., in particular 50-70° C.), in order to add said compound to the stabilizing envelope. This alternative embodiment is particularly useful to subsequently introduce into the stabilizing layer amphiphilic compounds which may otherwise negatively affect the properties of the final product if introduced in the initial mixture of the emulsion. Examples of amphiphilic compounds which can conveniently be subsequently introduced as additional components of the stabilizing envelope after the preparation of the initial emulsion are, for instance, PEG-modified phospholipids, in particular PEG-modified phosphatidylethanolamines, such as DMPE-PEG750, DMPE-PEG1000, DMPE-PEG2000, DMPE-PEG3000, DMPE-PEG4000, DMPE-PEG5000, DPPE-PEG750, DPPE-PEG1000, DPPE-PEG2000, DPPE-PEG3000, DPPE-PEG4000, DPPE-PEG5000, DSPE-PEG750, DSPE-PEG1000, DSPE-PEG2000, DSPE-PEG3000, DSPE-PEG4000, DSPE-PEG5000, DAPE-PEG750, DAPE-PEG1000, DAPE-PEG2000, DAPE-PEG3000, DAPE-PEG4000 or DAPE-PEG5000. Similarly, also PEG-modified phospholipids bearing reactive moieties or targeting ligands (e.g. containing biotin, maleimide, or maleimide-peptide) can conveniently be introduced subsequently according to this method. In addition, this technique can also be used to subsequently add to the composition of the stabilizing layer other components, such as lipopeptides or polymeric surfactants. Examples of polymeric surfactants which can be conveniently added after formation of the emulsion are, for instance, ethyleneoxide-propylenoxide block copolymers, such as Pluronic F68, Pluronic F108, Pluronic F-127 (Sigma Aldrich, Mo., USA); Polyoxyethylated alkyl ethers such as Brij® 78 (Sigma Aldrich, Mo., USA); Polyoxyethylene fatty acid esters such as Myrj® 53 or Myrj® 59 (Sigma Aldrich, Mo., USA); Polyoxyethylenesorbitan fatty acid ester such as Tween® 60 (Sigma Aldrich, Mo., USA); or Polyethylene glycol tert-octylphenyl ether such as Triton®X-100 (Sigma Aldrich, Mo., USA).

The Applicant has in fact observed that the use of a mixture containing limited amounts (e.g. less than 10% by weight) of a PEG modified phospholipid (e.g. DSPE-PEG or DPPE-PEG) together with a film forming phospholipid (e.g. DPPS or a 50:50 mixture of DAPC/DPPS) for preparing an emulsion according to the process of the invention, may determine a substantial broadening of the size distribution in the final product, with respect to the size distribution of microbubbles obtained from an emulsion containing only the film forming phospholipid. On the other side, if an emulsion containing only the film forming phospholipid is first prepared and then an aqueous suspension of the PEG modified phospholipid is subsequently added to the obtained emulsion (e.g. under agitation for 1 hour, at a temperature of about 60° C.), it has been observed that a rather high amount (typically more than 30% by weight) of the PEG modified phospholipid can be incorporated into the stabilizing envelope, without substantially affecting the size distribution of the final product.

According to a preferred embodiment, the emulsion is subjected to a controlled additional heating treatment before the lyophilization step. The additional heating of the emulsion is preferably performed into a sealed container. The heat treatment can vary from about 15 minutes to about 90 minutes, at temperatures comprised from about 60° C. to about 125° C., preferably from about 80° C. to about 120° C. In general, the higher the temperature, the shortest the time of the thermal treatment. During the heating, the emulsion can optionally be kept under agitation.

As observed by the Applicant, while this additional thermal treatment may result in a partial degradation of the phospholipids (e.g. with a content of about 5-20% w/w of lysolipids in the final product, when the emulsion is heated at about 100-120° C. for about 30 min), it has nevertheless the great advantage of allowing a substantial narrowing of the size distribution and an increase of the total number of microbubbles in the final suspension, independently from the working conditions of the initial emulsification step (e.g. type of organic solvent, emulsifying technique, optional washing steps, etc.).

The thermally treated emulsion can then be directly subjected to lyophilization, typically without the need of further washing steps.

Lyophilization of the emulsion according to step b) may be carried out by initially freezing the emulsion and thereafter lyophilizing the frozen emulsion, by per se generally known methods and devices. Since the dried, lyophilized, product will normally be reconstituted by addition of a carrier liquid prior to administration, the emulsion may advantageously be filled into sealable vials prior to lyophilization so as to give vials each containing an appropriate amount, e.g. a single dosage unit, of lyophilized dried product for reconstitution into an injectable form. By lyophilizing the emulsion in individual vials rather than in bulk, handling of the delicate honeycomb-like structure of the lyophilized product and the risk of at least partially degrading this structure are avoided.

Following lyophilization, the vacuum can be removed in the lyophilizer by introducing the desired gas to form the microbubbles in the final formulation of the contrast agent. This will allow to fill the headspace of the vials with the desired gas and then seal the vials with an appropriate closure. Alternatively, the vial can be kept under vacuum and sealed, while the gas is added at a later stage, e.g. just before administration, for instance when the gas is a radioactive or a hyperpolarized gas.

The so obtained lyophilized product in the presence of the suitable gas can thus be stably stored for several months before being reconstituted by dissolving it into an aqueous carrier liquid, to obtain a suspension of gas-filled microbubbles.

Any biocompatible gas, gas precursor or mixture thereof may be employed to fill the above microvesicles, the gas being selected depending on the chosen modality.

The gas may comprise, for example, air; nitrogen; oxygen; carbon dioxide; hydrogen; nitrous oxide; a noble or inert gas such as helium, argon, xenon or krypton; a radioactive gas such as $Xe^{133}$ or $Kr^{81}$; a hyperpolarized noble gas such as hyperpolarized helium, hyperpolarized xenon or hyperpolarized neon; a low molecular weight hydrocarbon (e.g. containing up to 7 carbon atoms), for example an alkane such as methane, ethane, propane, butane, isobutane, pentane or isopentane, a cycloalkane such as cyclobutane or cyclopentane, an alkene such as propene, butene or isobutene, or an alkyne such as acetylene; an ether; a ketone; an ester; halogenated gases, preferably fluorinated gases, such as or halogenated, fluorinated or perfluorinated low molecular weight hydrocarbons (e.g. containing up to 7 carbon atoms); or a mixture of any of the foregoing. Where a halogenated hydrocarbon is used, preferably at least some, more preferably all, of the halogen atoms in said compound are fluorine atoms.

Fluorinated gases are preferred, in particular perfluorinated gases, especially in the field of ultrasound imaging. Fluorinated gases include materials which contain at least one fluorine atom such as, for instance fluorinated hydrocarbons (organic compounds containing one or more carbon atoms and fluorine); sulfur hexafluoride; fluorinated, preferably perfluorinated, ketones such as perfluoroacetone; and fluorinated, preferably perfluorinated, ethers such as perfluorodiethyl ether. Preferred compounds are perfluorinated gases, such as $SF_6$ or perfluorocarbons (perfluorinated hydrocarbons), i.e. hydrocarbons where all the hydrogen atoms are replaced by fluorine atoms, which are known to form particularly stable microbubble suspensions, as disclosed, for instance, in EP 0554 213, which is herein incorporated by reference.

The term perfluorocarbon includes saturated, unsaturated, and cyclic perfluorocarbons. Examples of biocompatible, physiologically acceptable perfluorocarbons are: perfluoroalkanes, such as perfluoromethane, perfluoroethane, perfluoropropanes, perfluorobutanes (e.g. perfluoro-n-butane, optionally in admixture with other isomers such as perfluoroisobutane), perfluoropentanes, perfluorohexanes or perfluoroheptanes; perfluoroalkenes, such as perfluoropropene, perfluorobutenes (e.g. perfluorobut-2ene) or perfluorobutadiene; perfluoroalkynes (e.g. perfluorobut-2-yne); and perfluorocycloalkanes (e.g. perfluorocyclobutane, perfluoromethylcyclobutane, perfluorodimethylcyclobutanes, perfluorotrimethylcyclobutanes, perfluorocyclopentane, perfluoromethylcyclopentane, perfluorodimethylcyclopentanes, perfluorocyclohexane, perfluoromethylcyclohexane and perfluorocycloheptane). Preferred saturated perfluorocarbons have the formula $C_nF_{n+2}$, where n is from 1 to 12, preferably from 2 to 10, most preferably from 3 to 8 and even more preferably from 3 to 6. Suitable perfluorocarbons include, for example, $CF_4$, $C_2F_6$, $C_3F_8$, $C_4F_8$, $C_4F_{10}$, $C_5F_{12}$, $C_6F_{12}$, $C_6F_{14}$, $C_7F_{14}$, $C_7F_{16}$, $C_8F_{18}$, and $C_9F_{20}$.

Particularly preferred gases are $SF_6$ or perfluorocarbons selected from $CF_4$, $C_2F_6$, $C_3F_8$, $C_4F_8$, $C_4F_{10}$ or mixtures thereof; $SF_6$, $C_3F_8$ or $C_4F_{10}$ are particularly preferred.

It may also be advantageous to use a mixture of any of the above gases in any ratio. For instance, the mixture may comprise a conventional gas, such as nitrogen, air or carbon dioxide and a gas forming a stable microbubble suspension, such as sulfur hexafluoride or a perfluorocarbon as indicated above. Examples of suitable gas mixtures can be found, for instance, in WO 94/09829, which is herein incorporated by reference. The following combinations are particularly preferred: a mixture of gases (A) and (B) in which the gas (B) is a fluorinated gas, preferably selected from $SF_6$, $CF_4$, $C_2F_6$, $C_3F_6$, $C_3F_8$, $C_4F_6$, $C_4F_8$, $C_4F_{10}$, $C_5F_{10}$, $C_5F_{12}$ or mixtures thereof, and (A) is selected from air, oxygen, nitrogen, carbon dioxide or mixtures thereof. The amount of gas (B) can represent from about 0.5% to about 95% v/v of the total mixture, preferably from about 5% to 80%.

In some instances it may be desirable to include a precursor to a gaseous substance (i.e. a material that is capable of being converted to a gas in vivo). Preferably the gaseous precursor and the gas derived therefrom are physiologically acceptable. The gaseous precursor may be pH-activated, photo-activated, temperature activated, etc. For example, certain perfluorocarbons may be used as temperature activated gaseous precursors. These perfluorocarbons, such as perfluoropentane or perfluorohexane, have a liquid/gas phase transition temperature above room temperature (or the temperature at which the agents are produced and/or stored) but below body temperature; thus, they undergo a liquid/gas phase transition and are converted to a gas within the human body. Furthermore, the term "gas" as used herein includes mixtures in vapor form at the normal human body temperature of 37° C. Compounds which at the temperature of 37° C. are liquid may thus also be used in limited amounts in admixture with other gaseous compounds, to obtain a mixture which is in a vapor phase at 37° C.

For ultrasonic echography, the biocompatible gas or gas mixture is preferably selected from air, nitrogen, carbon dioxide, helium, krypton, xenon, argon, methane, halogenated hydrocarbons (including fluorinated gases such as perfluorocarbons and sulfur hexafluoride) or mixtures thereof. Advantageously, perfluorocarbons (in particular $C_4F_{10}$ or $C_3F_8$) or $SF_6$ can be used, optionally in admixture with air or nitrogen.

For the use in MRI the microbubbles will preferably contain a hyperpolarized noble gas such as hyperpolarized neon, hyperpolarized helium, hyperpolarized xenon, or mixtures thereof, optionally in admixture with air, $CO_2$, oxygen, nitrogen, helium, xenon, or any of the halogenated hydrocarbons as defined above.

For use in scintigraphy, the microbubbles according to the invention will preferably contain radioactive gases such as $Xe^{133}$ or $Kr^{81}$ or mixtures thereof, optionally in admixture with air, $CO_2$, oxygen, nitrogen, helium, kripton or any of the halogenated hydrocarbons as defined above.

The lyophilized composition in contact with the gas can then be very easily reconstituted by the addition of an appropriate sterile aqueous injectable and physiologically acceptable carrier liquid such as sterile pyrogen-free water for injection, an aqueous solution such as saline (which may advantageously be balanced so that the final product for injection is not hypotonic), or an aqueous solution of one or more tonicity-adjusting substances such as salts (e.g. of plasma cations with physiologically tolerable counterions), or sugars, sugar alcohols, glycols and other non-ionic polyol materials (e.g. glucose, sucrose, sorbitol, mannitol, glycerol, polyethylene glycols, propylene glycols and the like), requiring only minimal agitation such as may, for example, be provided by gentle hand-shaking.

As observed by the Applicant, the so obtained reconstituted microbubbles have generally a number mean diameter which is slightly lower than the number mean diameter measured for the microdroplets of the emulsion. The mean number diameter of the microbubbles is in general from about 60% to about 90% of the mean number diameter of the emulsion's microdroplets. In most cases, a mean number diameter of the microbubbles of about 70-75% of the mean number diameter of the microdroplets has been observed.

Where the dried product is contained in a vial, this is conveniently sealed with a septum through which the carrier liquid may be injected using an optionally pre-filled syringe; alternatively the dried product and carrier liquid may be supplied together in a dual chamber device such as a dual chamber syringe. It may be advantageous to mix or gently shake the product following reconstitution. However, as noted above, in the stabilized contrast agents according to the invention the size of the gas microbubbles may be substantially independent of the amount of agitation energy applied to the reconstituted dried product. Accordingly no more than gentle handshaking may be required to give reproducible products with consistent microbubble size.

The microbubble suspensions generated upon reconstitution in water or an aqueous solution may be stable for at least 12 hours, thus permitting considerable flexibility as to when the dried product is reconstituted prior to injection.

Unless it contains a hyperpolarized gas, known to require special storage conditions, the lyophilised residue may be stored and transported without need of temperature control of its environment and in particular it may be supplied to hospitals and physicians for on site formulation into a ready-to-use administrable suspension without requiring such users to have special storage facilities.

Preferably in such a case it can be supplied in the form of a two component kit.

Said two component kit can include two separate containers or a dual-chamber container. In the former case preferably the container is a conventional septum-sealed vial, wherein the vial containing the lyophilized residue of step b) is sealed with a septum through which the carrier liquid may be injected using an optionally prefilled syringe. In such a case the syringe used as the container of the second component is also used then for injecting the contrast agent. In the latter case, preferably the dual-chamber container is a dual-chamber syringe and once the lyophilisate has been reconstituted and then suitably mixed or gently shaken, the container can be used directly for injecting the contrast agent. In both cases means for directing or permitting application of sufficient bubble forming energy into the contents of the container are provided. However, as noted above, in the stabilised contrast agents according to the invention the size of the gas microbubbles is substantially independent of the amount of agitation energy applied to the reconstituted dried product. Accordingly no more than gentle hand shaking is generally required to give reproducible products with consistent microbubble size.

It can be appreciated by one ordinary skilled in the art that other two-chamber reconstitution systems capable of combining the dried powder with the aqueous solution in a sterile manner are also within the scope of the present invention. In such systems, it is particularly advantageous if the aqueous phase can be interposed between the water-insoluble gas and the environment, to increase shelf life of the product. Where a material necessary for forming the contrast agent is not already present in the container (e.g. a targeting ligand to be linked to the phospholipid during reconstitution), it can be packaged with the other components of the kit, preferably in a form or container adapted to facilitate ready combination with the other components of the kit.

No specific containers, vial or connection systems are required; the present invention may use conventional containers, vials and adapters. The only requirement is a good seal between the stopper and the container. The quality of the seal, therefore, becomes a matter of primary concern; any degradation of seal integrity could allow undesirables substances to enter the vial. In addition to assuring sterility, vacuum retention is essential for products stoppered at ambient or reduced pressures to assure safe and proper reconstitution. As to the stopper, it may be a compound or multicomponent formulation based on an elastomer, such as poly(isobutylene) or butyl rubber.

The contrast agents obtainable by the process of the present invention may be used in a variety of diagnostic imaging techniques, including in particular ultrasound and Magnetic Resonance. Possible other diagnostic imaging applications include scintigraphy, light imaging, and X-ray imaging, including X-ray phase contrast imaging.

Their use in diagnostic ultrasound imaging and in MR imaging, e.g. as susceptibility contrast agents and as hyperpolarized gas bubbles, constitute preferred features of the invention. A variety of imaging techniques may be employed in ultrasound applications, for example including fundamental and harmonic B-mode imaging, pulse or phase inversion imaging and fundamental and harmonic Doppler imaging; if desired three-dimensional imaging techniques may be used.

In vivo ultrasound tests in rabbits, dogs and pigs have shown that contrast agents according to the invention may produce an increase in backscattered signal intensity from the myocardium of 15-25 dB following intravenous injection of doses as low as 0.001 ml/kg body weight. Signals may be observed at even lower doses using more sensitive techniques such as color Doppler or power pulse inversion. At these low doses, attenuation in blood-filled compartments such as the heart chambers has been found to be sufficiently low to permit visualization of regions of interest in the myocardial vasculature. Tests have also shown such intravenously injected contrast agents to be distributed throughout the whole blood pool, thereby enhancing the echogenicity of all vascularised tissues, and to be recirculated. They have also been found useful as general Doppler signal enhancement aids, and may additionally be useful in ultrasound-computed tomography and in physiologically triggered or intermittent imaging.

For ultrasound applications such as echocardiography, in order to permit free passage through the pulmonary system and to achieve resonance with the preferred imaging frequencies of about 0.1-15 MHz, microbubbles having an average size of 0.1-10 μm, e.g. 0.5-7 μm are generally employed. As described above, contrast agents according to the invention may be produced with a very narrow size distribution for the microbubble dispersion within the range preferred for echocardiography, thereby greatly enhancing their echogenicity as well as their safety in vivo, and rendering the contrast agents of particular advantage in applications such as blood pressure measurements, blood flow tracing and ultrasound tomography.

In ultrasound applications the contrast agents of the invention may, for example, be administered in doses such that the amount of phospholipid Injected is in the range 0.1-200 μg/kg body weight, typically 10-200 μg/kg in the absence of a washing step for the emulsion and 0.1-30 μg/kg if the emulsion has been washed prior to lyophilisation. It will be appreciated that the use of such low levels of phospholipid is of substantial advantage in minimising possible toxic side effects. Furthermore, the low levels of phospholipids present in effective doses may permit dosage increases to prolong observation times without adverse effects.

According to a preferred embodiment of the invention, the process of the invention allows to obtain small diameter gas-filled microbubbles showing an extremely narrow size distribution. Thus, by suitably selecting the components of the mixture and in particular the amount of agitation energy applied during the emulsion of the aqueous-organic mixture, it is possible to obtain gas-filled microbubbles with the desired numerical mean diameter and size distribution.

In particular, by exploiting the process according to the present invention it is possible to obtain contrast agents comprising phospholipid-stabilized small-sized gas microbubbles characterized by having relatively small mean dimensions and a particularly useful narrow and controlled size distribution.

As known by those skilled in the art, the dimensions of micro/nano particles and their respective size distribution can be characterized by a number of parameters, the most frequently used being the mean diameter in number $D_N$, the median diameter in number $D_{N50}$, the mean diameter in volume $D_V$ and the median diameter in volume $D_{V50}$. While diameters in number provide an indication of the mean number dimension of the particles, the diameter in volume provides information on how the total volume of the particles is distributed among the whole population. As the presence of very few large volume particles in a population of otherwise small volume particles may cause the corresponding $D_V$ value to be shifted towards high values, it is sometimes more convenient to use the $D_{V50}$ value for evaluating the distribution of a particles' population. $D_{V50}$ is a calculated value indicating that half of the total of particles' internal volume is present in particles having a diameter lower than $D_{V50}$; this allows to reduce the effects of accidentally formed large volume particles in the evaluation of the size distribution. Clearly, mono-sized particles show identical $D_N$, $D_{N50}$, $D_V$ and $D_{V50}$ values. On the other side, an increasing broadening of particles' distribution will result in a larger difference between these various values with a corresponding variation of the respective ratio thereof (e.g. increase of $D_V/D_N$ ratio). For example, particles populations containing primarily small particles (e.g. particles with a diameter around 2 µm) with nevertheless a small percentage of large particles (for instance particles with a diameter above 8 µm) show higher $D_V$ or $D_{V50}$ values as compared to the $D_N$ value, with correspondingly higher $D_V/D_N$ or $D_{V50}/D_N$ ratios.

The process of the present invention has thus been found particularly suitable to prepare microbubbles having a mean diameter in number ($D_N$) of less than 1.70 µm and a median diameter in volume ($D_{V50}$) such that the $D_{V50}/D_N$ ratio is of about 2.30 or lower, preferably lower than 2.10. Preferably said $D_N$ value is of 1.60 µm or lower, more preferably of 1.50 µm or lower, much more preferably of 1.30 µm or lower. Microbubbles with lower values of $D_N$, e.g. of about 1 µm, or even lower, e.g. 0.85 µm and down to 0.80 µm, can easily be obtained with the process of the invention. The $D_{V50}/D_N$ ratio is preferably of about 1.80 or lower, more preferably of about 1.60 or lower, much more preferably of about 1.50 or lower. Microbubbles with lower values of the $D_{V50}/D_N$ ratio, e.g. 1.20, and even lower, e.g. 1.05, can easily be obtained.

Furthermore, in the suspensions of small size narrowly-distributed microbubbles obtainable according to the process of the invention, it has been observed that the amount of microbubbles with a diameter larger than 3 µm (expressed as the percentage of particles over the total number of particles), in particular for microbubbles having a $D_N$ lower than about 1.5 µm and a $D_{V50}/D_N$ ratio of less than about 2.00, is typically lower than about 3% with respect to the total number of microbubbles in the suspension, preferably lower than about 2%, more preferably lower than about 1%. The concentration of microbubbles in the reconstituted suspension is in general of at least $1 \times 10^8$ particles per milliliter, preferably of at least $1 \times 10^9$ particles per milliliter.

The above values of $D_{V50}$, $D_N$ and number of microbubbles are referred to a measurement made by using a Coulter Counter Mark II apparatus fitted with a 30 µm aperture, with a measuring range of 0.7 to 20 µm.

This specific category of contrast agents are particularly valuable in ultrasound imaging, in particular for imaging techniques relying on non-linear scattering of microbubbles, as explained below.

Most recent ultrasound contrast-imaging methods exploit the nonlinear scattering characteristics of ultrasound contrast agents. From the literature (e.g. Eatock et al., Journal of the Acoustical Society of America, vol. 77 (5), pp 1692-1701, 1985) it is known that nonlinear scattering is significant only for microbubbles which are smaller than, or close to, resonance size. In particular, microbubbles with dimensions of half the resonance size can conveniently be employed. "Half the resonance size" is the size of a microbubble with a resonance frequency that equals twice the centre frequency of the transmitted ultrasound wave (which for particular applications may be of up to about 60 MHz). When imaging a volume containing a microbubble-based ultrasound contrast agent, the detectability of the microbubble echoes against tissue echoes is enhanced by the level of nonlinear scattering by the microbubbles, and decreased by the attenuation caused by the microbubbles located between the probe and the region of interest. Attenuation along the transmit path reduces the ultrasound-energy available for generating nonlinear bubble-response; attenuation along the receive path removes echo-energy able to reach the ultrasound probe. In the case of a suspension comprising a wide range of microbubble sizes, the microbubbles at resonance size, and larger than resonance size, mainly contribute to transmit-receive attenuation, without contributing in an efficient way to the nonlinear echo signals. Therefore, the overall acoustic response for nonlinear imaging greatly benefits from the use of a calibrated set of microbubbles having a narrow size distribution and a mean size close to half the resonance size. Preferably, microbubbles preparations having a size distribution corresponding to a $D_{V50}/D_N$ ratio of about 2.30 or lower, more preferably of 2.10 or lower and much more preferably of 2.00 or lower are employed. Preferably, the mean size of the employed microbubbles is of about ±10% of half the resonance size, more preferably of about ±5% of half the resonance size.

A yet still further aspect of the present invention thus relates to a method of diagnostic imaging which comprises administering to a subject a contrast-enhancing amount of a contrast agent comprising gas-filled microbubbles with the size and size distribution as above specified and imaging at least a part of said subject. In particular, said diagnostic imaging includes insonating said subject by means of an ultrasound device generating an ultrasound wave with a predetermined transmit frequency, from which a corresponding resonance size of microbubbles is determined, and administering a contrast agent comprising gas-filled microbubbles having a narrow size distribution and a mean size close to half the resonance size. Preferably, the narrow size distribution and a mean size of the microbubbles are as above defined. For instance, a HDI 5000 ultrasound machine from Philips (e.g. in pulse inversion mode, with L7-4 probe and Mechanical Index of 0.07), can be used in the diagnostic imaging method. According to this method, said subject is a vertebrate and said contrast agent is introduced into the vasculature or into a body cavity of said vertebrate. Said contrast agent can be supplied as a kit, such as those previously described, comprising the lyophilized product in contact with the gas and an aqueous medium for reconstitution.

The following non-limitative examples are given for better illustrating the invention.

EXAMPLES

The following materials have been employed in the following examples.

| PHOSPHOLIPIDS: | |
|---|---|
| DPPS | Dipalmitoylphosphatidylserine (Genzyme) |
| | IUPAC: 1,2-Dipalmitoyl-sn-glycero-3-phosphocholine |
| DPPG | Dipalmitoylphosphatidylglycerol sodium salt (Genzyme) |
| | IUPAC: 1,2-Dipalmitoyl-sn-glycero-3-[phospho-rac-(1-glycerol)] |
| DSPA | Distearoyl phosphatidic acid sodium salt (Genzyme) |
| | IUPAC: 1,2-Distearoyl-sn-glycero-3-phosphate |
| DSPG | Distearoylphosphatidylglycerol sodium salt (Genzyme) |
| | IUPAC: 1,2-Distearoyl-sn-glycero-3-phosphoserine) |
| DSPC | Distearoylphosphatidylcholine (Genzyme) |
| | IUPAC: 1,2-Distearoyl-sn-glycero-3-phosphocholine |
| DSEPC | Distearoylethylphosphatidylcholine (Avanti Polar Lipids) |
| | IUPAC: 1,2-Distearoyl-sn-glycero-3-Ethylphosphocholine |
| DAPC | Diarachidoylphosphatidylcholine (Avanti polar Lipids) |
| | IUPAC: 1,2-Diarachidoyl-sn-glycero-3-phosphocholine |
| DSTAP | 1,2-Distearoyl-3-trimethylammonium-propane chloride (Avanti Polar Lipids) |
| DSPE-PEG2000 | Distearoylphosphatidylethanolamine modified with PEG2000, sodium salt (Nektar Therapeutics) |
| DSPE-PEG5000 | Distearoylphosphatidylethanolamine modified with PEG5000, sodium salt (Nektar Therapeutics) |
| DSPE-PEG2000-maleimid | Distearoylphosphatidylethanolamine modified with PEG2000-maleimide (Avanti Polar lipids) |
| SATA | N-Succinimidyl-S-acetylthioacetate (Pierce) |
| RGD-4C | H-Ala-Cys-Asp-Cys-Arg-Gly-Asp-Cys-Phe-Cys-Gly-NH$_2$ (AnaSpec Inc.) |

Solvents:
  Perfluoro-n-hexane ($C_6F_{14}$), by Fluka
  perfluoromethylcyclohexane ($CF_3$-cyclo-$C_6F_{11}$), by Fluka
  perfluoro-n-heptane ($C_7F_{16}$), by Fluka
  perfluoro-n-nonane ($C_9F_{20}$), by Aldrich
  perfluorodecalin, by Aldrich
  Cyclohexane, by Fluka
  Cyclooctane, by Fluka
  n-Decane, by Fluka
  n-Octane, by Fluka
  meta xylene, by Fluka
  Diisopropyl cetone, by Fluka
  $CCl_4$, by Fluka
Lyoprotectants:
  Mannose, by Fluka
  Glucose, by Fluka
  Sorbitol, by Fluka
  Mannitol, by Fluka
  Maltose, by Fluka
  Dextran 6000, by Fluka
  Dextran 15000, by Fluka
  Dextran 40000, by Fluka
  Inulin, by Fluka
Characterization of Microdroplets and Microbubbles.

The size distribution of the emulsions microdroplets has been determined:
  a) by means of a Coulter counter (Counter Mark II apparatus fitted with a 30 µm aperture with a measuring range of 0.7 to 20 µm), when the emulsion has been submitted to a washing step; 10 µl of emulsion were diluted in 100 ml of saline at room temperature and allowed to equilibrate for 3 minutes prior to measurement;
  b) by means of a laser light scattering particle sizer (Malvern Mastersizer, dilution 200×, focal length 45 mm, standard presentation), if the emulsion has not been subjected to a washing step.

The size distributions, volume concentrations and number of the microbubbles (after lyophilisation and reconstitution with an aqueous phase) were determined by using a Coulter Counter Mark II apparatus fitted with a 30 µm aperture with a measuring range of 0.7 to 20 µm. 50 µl of microbubble samples were diluted in 100 ml of saline at room temperature and allowed to equilibrate for 3 minutes prior to measurement.

The amounts of phospholipids in the final preparations (emulsion of microbubbles suspension) were determined by HPLC-MS analysis, with the following set up: Agilent 1100 LC chromatograph, MN CC 125/2 mm-5 C8 column from Maherey Nagel, Agilent MSD G1946D detector.

Lyophilization

The lyophilization methodology and apparatus were as follows. The emulsion (optionally after the washing step, if present) is first frozen at −45° C. for 5 minutes and then freeze-dried (lyophilized) at room temperature at a pressure of 0.2 mbar, by using a Christ-Alpha 2-4 freeze-drier.

Example 1

Preparations 1a-1n 10 mg of DPPS are added to about 10 ml of an 10% (w/w) mannitol aqueous solution; the suspension is heated at 65° C. for 15 minutes and then cooled at room temperature (22° C.). Perfluoroheptane (8% v/v) is added to this aqueous phase and emulsified in a beaker of about 4 cm diameter by using a high speed homogenizer (Polytron T3000, probe diameter of 3 cm) for 1 minute at the speed indicated in table 1. The resulting median diameter in volume ($D_{V50}$) and a mean diameter in number ($D_N$) of microdroplets of the emulsion are shown in table 1. The emulsion is then centrifuged (800-1200 rpm for 10 minutes, Sigma centrifuge 3K10) to eliminate the excess of the phospholipid and the separated pellets (microdroplets) were recovered and re-suspended in the same initial volume of a 10% mannitol aqueous solution.

The washed emulsion is then collected into a 100 ml balloon for lyophilization, frozen and then freeze-dried according to the above standard procedure. The lyophilized is then exposed to an atmosphere containing 35% of perfluoro-n-butane and 65% of nitrogen and then dispersed in a volume of water twice than the initial one by gentle hand shaking. The microbubble suspension obtained after reconstitution with distilled water is analyzed using a Coulter counter. The concentration of microbubbles in the obtained suspensions was of about 1×10$^9$ particles per ml. The respective microbubbles median diameter in volume ($D_{V50}$), mean diameter in volume ($D_V$), mean diameter in number ($D_N$) an the amount of microbubbles with diameter larger than 3 µm (percentage over the total number of microbubbles) are given in table 1. When more than one example has been performed at the same agitation speed, the values indicated in table 1 are referred to the mean calculated value of each parameter.

TABLE 1

| Ex. | EMULSION Agitation (rpm) | $D_{V50}$ (μm) | $D_N$ (μm) | Gas-filled microbubbles $D_{V50}$ (μm) | $D_V$ (μm) | $D_N$ (μm) | $D_{V50}/D_N$ | >3 μm (%) |
|---|---|---|---|---|---|---|---|---|
| 1a | 8000 | 4.58 | 1.77 | 2.92 | 3.33 | 1.51 | 1.93 | 5.44 |
| 1b | 9000 | 4.66 | 1.94 | 3.19 | 3.45 | 1.53 | 2.08 | 6.61 |
| 1c | 10000 | 3.04 | 1.74 | 2.16 | 2.53 | 1.33 | 1.62 | 1.88 |
| 1d | 11000 | 3.05 | 1.80 | 2.17 | 3.33 | 1.32 | 1.65 | 1.55 |
| 1e | 12000 | 2.84 | 1.69 | 1.86 | 2.17 | 1.24 | 1.50 | 0.93 |
| 1f | 12500 | 2.79 | 1.68 | 1.75 | 2.05 | 1.22 | 1.44 | 0.65 |
| 1g | 14000 | 2.20 | 1.52 | 1.39 | 2.45 | 1.08 | 1.29 | 0.23 |
| 1h | 14500 | 2.00 | 1.38 | 1.19 | 1.39 | 1.01 | 1.19 | 0.06 |
| 1i | 15000 | 1.88 | 1.39 | 1.22 | 2.20 | 1.01 | 1.21 | 0.06 |
| 1j | 15500 | 2.19 | 1.48 | 1.24 | 1.46 | 1.02 | 1.22 | 0.11 |
| 1k | 16000 | 1.83 | 1.32 | 1.27 | 3.08 | 0.99 | 1.28 | 0.10 |
| 1l | 17000 | 1.40 | 1.12 | 0.91 | 1.03 | 0.87 | 1.05 | 0.01 |

Example 2

Preparations 2a-2j

The same procedure adopted for example 1 is followed, with the only difference that the phospholipid is a mixture of DPPS (20% w/w) and DSPC (80% w/w), the total amount of phospholipid remaining unchanged. The results are summarized in table 2.

TABLE 2

| Ex. | EMULSION Agitation (rpm) | $D_{V50}$ (μm) | $D_N$ (μm) | Gas-filled microbubbles $D_{V50}$ (μm) | $D_V$ (μm) | $D_N$ (μm) | $D_{V50}/D_N$ | >3 μm (%) |
|---|---|---|---|---|---|---|---|---|
| 2a | 6000 | 8.75 | 3.07 | 7.55 | 9.05 | 2.27 | 3.33 | 21.81 |
| 2b | 10000 | 3.54 | 1.90 | 3.00 | 3.71 | 1.47 | 2.04 | 5.05 |
| 2c | 12000 | 3.04 | 1.83 | 2.45 | 3.73 | 1.32 | 1.85 | 2.15 |
| 2d | 12500 | 2.85 | 1.76 | 2.21 | 3.24 | 1.27 | 1.74 | 1.57 |
| 2e | 13000 | 2.98 | 1.83 | 2.25 | 3.04 | 1.28 | 1.76 | 1.76 |
| 2f | 13500 | 2.91 | 2.05 | 1.88 | 2.46 | 1.20 | 1.57 | 0.87 |
| 2g | 14000 | 2.45 | 1.67 | 1.82 | 2.66 | 1.16 | 1.57 | 0.57 |
| 2h | 14500 | 2.18 | 1.55 | 1.58 | 3.04 | 1.09 | 1.44 | 0.38 |
| 2i | 15000 | 1.94 | 1.42 | 1.34 | 1.96 | 1.04 | 1.28 | 0.31 |
| 2j | 16000 | 1.81 | 1.38 | 1.35 | 2.30 | 1.03 | 1.31 | 0.14 |

Example 3

Preparation 3a-3p

The same procedure adopted for examples 2 is followed, with the only difference that the DPPS/DSPC weight ratio is varied, as reported in table 3. The results are summarized in table 3.

TABLE 3

| Ex. | DPPS/DSPC ratio | EMULSION Agitation (rpm) | $D_{V50}$ (μm) | $D_N$ (μm) | Gas-filled microbubbles $D_{V50}$ (μm) | $D_N$ (μm) | $D_{V50}/D_N$ | >3 μm (%) |
|---|---|---|---|---|---|---|---|---|
| 3a | 80/20 | 12000 | 2.44 | 1.54 | 1.68 | 1.19 | 1.41 | 0.48 |
| 3b | 75/25 | 12000 | 2.53 | 1.66 | 1.73 | 1.18 | 1.47 | 0.62 |
| 3c | 60/40 | 11000 | 3.53 | 1.86 | 2.75 | 1.45 | 1.90 | 4.00 |
| 3d | 60/40 | 12000 | 2.62 | 1.60 | 1.78 | 1.21 | 1.47 | 0.72 |
| 3e | 60/40 | 14000 | 2.36 | 1.60 | 1.59 | 1.13 | 1.41 | 0.36 |
| 3f | 50/50 | 12000 | 2.81 | 1.68 | 2.28 | 1.30 | 1.75 | 2.05 |
| 3g | 40/60 | 11000 | 3.00 | 1.72 | 2.44 | 1.32 | 1.85 | 2.31 |
| 3h | 40/60 | 12000 | 2.88 | 1.75 | 2.07 | 1.27 | 1.63 | 1.45 |
| 3i | 40/60 | 13000 | 2.61 | 1.69 | 1.76 | 1.16 | 1.52 | 0.57 |
| 3j | 40/60 | 14000 | 2.06 | 1.43 | 1.41 | 1.07 | 1.31 | 0.23 |
| 3k | 40/60 | 14500 | 2.39 | 1.67 | 1.64 | 1.15 | 1.43 | 0.49 |
| 3l | 30/70 | 11000 | 3.12 | 1.75 | 2.64 | 1.37 | 1.93 | 2.76 |
| 3m | 30/70 | 12000 | 3.08 | 1.81 | 2.38 | 1.34 | 1.78 | 2.45 |
| 3n | 25/75 | 11000 | 3.15 | 1.85 | 2.46 | 1.31 | 1.88 | 2.15 |
| 3o | 10/90 | 11000 | 3.72 | 2.26 | 3.14 | 1.47 | 2.13 | 4.60 |
| 3p | 5/95 | 11000 | 4.53 | 2.23 | 4.08 | 1.54 | 2.65 | 6.35 |

Example 4

The same procedure adopted for example 2 is followed, with the only difference that mixtures of DSPA and DPPS with different weight ratios were prepared. The results are summarized in table 4.

TABLE 4

| Ex. | DSPA/DPPS ratio | Emulsion Agitation (rpm) | $D_{V50}$ (μm) | $D_N$ (μm) | Gas-filled microbubbles $D_{V50}$ (μm) | $D_N$ (μm) | $D_{V50}/D_N$ | >3 μm (%) |
|---|---|---|---|---|---|---|---|---|
| 4a | 25/75 | 12000 | 2.61 | 1.63 | 1.94 | 1.24 | 1.56 | 1.07 |
| 4b | 50/50 | 11000 | 2.81 | 1.86 | 2.35 | 1.39 | 1.69 | 2.67 |
| 4c | 50/50 | 12000 | 2.35 | 1.57 | 1.84 | 1.19 | 1.55 | 0.74 |
| 4d | 75/25 | 12000 | 2.50 | 1.65 | 2.11 | 1.27 | 1.66 | 1.45 |

Example 5

Preparations 5a-5i

The same procedure adopted for example 1 is followed, with the only difference that a 1/1 (w/w) phospholipid mixture of DPPG and DSPC has been employed (total concentration 1.0 mg/ml) in admixture with 10% w/w (with respect to the total weight of phospholipid) of palmitic acid. The results are summarized in table 5.

TABLE 5

| Ex | EMULSION Agitation (rpm) | $D_{V50}$ (μm) | $D_N$ (μm) | Gas-filled microbubbles $D_{V50}$ (μm) | $D_N$ (μm) | $D_{V50}/D_N$ | >3 μm (%) |
|---|---|---|---|---|---|---|---|
| 5a | 6000 | 10.02 | 2.64 | 6.87 | 2.07 | 3.32 | 18.00 |
| 5b | 8000 | 5.31 | 2.49 | 3.73 | 1.62 | 2.30 | 7.97 |
| 5c | 9000 | 5.04 | 2.69 | 3.20 | 1.55 | 2.06 | 6.22 |
| 5d | 10000 | 3.82 | 2.02 | 2.85 | 1.38 | 2.07 | 2.65 |
| 5e | 10500 | 3.36 | 1.96 | 2.51 | 1.32 | 1.89 | 2.44 |
| 5f | 11000 | 3.22 | 1.87 | 2.31 | 1.28 | 1.81 | 1.41 |
| 5g | 12000 | 2.69 | 1.61 | 1.74 | 1.14 | 1.53 | 0.52 |
| 5h | 13000 | 2.28 | 1.56 | 1.56 | 1.07 | 1.46 | 0.23 |
| 5i | 14000 | 2.00 | 1.44 | 1.30 | 1.00 | 1.30 | 0.26 |

Example 6

The same procedure adopted for example 1 is followed, with the only difference that DSEPC is used as phospholipid and perfluorohexane is used as the organic solvent. The applied rotation speed is of 11000 rpm. Dimensions, size distribution and percentage of microbubbles with diameter larger than 3 μm were as follows.

| $D_{V50}$ (µm) | $D_N$ (µm) | $D_{V50}/D_N$ | >3 µm (%) |
|---|---|---|---|
| 1.65 | 1.11 | 1.49 | 0.30 |

Example 7

Preparations 7a-7l

Distilled water (10 ml) containing DPPS (10 mg) as phospholipid is heated at 70° C. for 15 minutes and then cooled at room temperature. 0.8 ml of an organic solvent as specified in the following table 6 were emulsified in this aqueous phase using a high speed homogenizer (Polytron T3000) at 10000 rpm for 1 minute. The emulsion is added to 10 ml of a 15% dextran 15000 solution, frozen and lyophilized (0.2 mbar, 24 hours). After lyophilisation, air is introduced in the lyophilizer. The microbubble suspension obtained after reconstitution with distilled water is analyzed using a Coulter counter. Table 6 summarizes the results in terms of dimensions and size distribution of microbubbles.

TABLE 6

| Ex. | Solvent | $D_{V50}$ (µm) | $D_N$ (µm) | $D_{V50}/D_N$ |
|---|---|---|---|---|
| 7a | $C_6F_{14}$ | 2.77 | 1.44 | 1.92 |
| 7b | $CF_3$-cyclo-$C_6F_{11}$ | 2.24 | 1.30 | 1.72 |
| 7c | $C_7F_{16}$ | 2.48 | 1.40 | 1.77 |
| 7d | $C_9F_{20}$ | 2.46 | 1.36 | 1.81 |
| 7e | perfluorodecalin | 3.76 | 1.52 | 2.47 |
| 7f | Cyclohexane | 2.61 | 1.41 | 1.85 |
| 7g | Cyclooctane | 2.43 | 1.35 | 1.80 |
| 7h | Decane | 2.01 | 1.12 | 1.79 |
| 7i | Octane | 2.87 | 0.96 | 2.99 |
| 7j | meta xylène | 2.45 | 1.21 | 2.02 |
| 7k | Diisopropyl cetone | 1.83 | 1.05 | 1.74 |
| 7l | $CCl_4$ | 1.90 | 1.27 | 1.50 |

Example 8

The above example 7 is repeated with the same methodology, by using perfluoro hexane as the organic solvent and different lyoprotecting agents at different concentrations as outlined in table 7. Table 7 summarizes the results in terms of dimensions and size distribution of microbubbles.

TABLE 7

| Ex. | Lyoprotectant and concentration (w/w) | $D_{V50}$ (µm) | $D_N$ (µm) | $D_{V50}/D_N$ |
|---|---|---|---|---|
| 8a | Mannose 5% | 4.35 | 1.90 | 2.29 |
| 8b | Glucose 5% | 2.59 | 0.96 | 2.70 |
| 8c | Sorbitol 5% | 3.84 | 1.40 | 2.74 |
| 8d | Mannitol 10% | 2.22 | 1.22 | 1.82 |
| 8e | Mannitol 5% | 2.24 | 1.21 | 1.85 |
| 8f | Mannitol 4% | 2.54 | 1.45 | 1.75 |
| 8g | Maltose 5% | 3.42 | 0.99 | 3.45 |
| 8h | Dextran 6000 7.5% | 3.30 | 1.48 | 2.23 |
| 8j | Dextran 15000 5% | 2.55 | 1.31 | 1.95 |
| 8k | Dextran 15000 7.5% | 2.77 | 1.44 | 1.92 |
| 8i | Dextran 40000 7.5% | 2.54 | 1.32 | 2.29 |
| 8l | Inulin 5% | 3.58 | 1.43 | 2.70 |

Example 9

Preparations 9a-9e

Example 1 is repeated by emulsifying the mixture at a speed of 10000 rpm. In addition, the same example is repeated by adding different amounts of Pluronic F68 (a poloxamer corresponding to Poloxamer 188) into the aqueous phase prior to emulsification, as outlined in table 8. Table 8 shows the results of the comparative experiment, in terms of size distribution and conversion yield of the microbubbles. Conversion yield is given as the percentage number of gas-filled microbubbles formed upon reconstitution of the lyophilized matrix with respect to the number of microdroplets measured in the emulsion.

TABLE 8

| Example | Pluronic* (mg/ml) | $D_{V50}$ | $D_N$ | $D_{V50}/D_N$ | Conversion yield (%) |
|---|---|---|---|---|---|
| 9a | 0 | 2.42 | 1.38 | 1.75 | 28.0 |
| 9b | 0.25 | 4.64 | 1.97 | 2.36 | 18.8 |
| 9c | 0.5 | 13.85 | 1.38 | 10.04 | 7.3 |
| 9d | 1.0 | 12.59 | 1.49 | 8.45 | 3.2 |
| 9e | 2.0 | 15.80 | 1.23 | 12.85 | 0.5 |

*Concentration referred to the volume of aqueous phase

The above results show that with a concentration of poloxamer corresponding to half the concentration of the phospholipid (i.e. about 33% of the total amount of surfactants in the mixture), both conversion yields and size distribution of microbubbles are negatively affected.

Example 10

Preparations 10a-10d

Example 9 is repeated, but instead of adding Pluronic F68 to the aqueous phase, different amounts of cholesterol (from Fluka) were added to the organic phase, prior to emulsification, as outlined in table 9. Table 9 shows the results of the comparative experiment, in terms of size distribution and conversion yield (from the microdroplets of the emulsion) of the microbubbles.

TABLE 9

| Example | Cholesterol* (mg/ml) | $D_{V50}$ | $D_N$ | $D_{V50}/D_N$ | Conversion yield (%) |
|---|---|---|---|---|---|
| 10a | 0 | 2.42 | 1.38 | 1.75 | 28.0 |
| 10b | 0.10 | 3.79 | 1.31 | 2.89 | 17.8 |
| 10c | 0.25 | 1.35 | 1.05 | 1.28 | 5.7 |
| 10d | 0.50 | 14.02 | 1.70 | 8.25 | 0.8 |

*Concentration referred to the volume of the aqueous phase

The above results show that with a concentration of 0.050% (w/w) of cholesterol in the aqueous phase, both conversion yield and size distribution of microbubbles are highly negatively affected. A concentration of 0.025%, while it may provide acceptable dimensions and size distribution of microbubbles, still results in a rather low conversion yield.

Example 11

Distilled water (30 ml) containing 60 mg of DPPS and 3 g of mannitol is heated to 70° C. during 15 minutes then cooled to room temperature.

Perfluoroheptane is emulsified in this aqueous phase using a high speed homogenizer (Polytron®, 12500 rpm, 1 minute).

The resulting emulsion, showing a median diameter in volume ($D_{V50}$) of 2.3 µm and a mean diameter in number ($D_N$) of 2.0 µm, is washed once by centrifugation, resuspended in 30 ml of a 10% solution of mannitol in distilled water and then divided in three portions (3×10 ml).

The first portion (A) is used as such for the subsequent lyophilization step. The second portion (B) is collected into a syringe and hand-injected through a 5 μm Nuclepore® filter (47 mm—Polycarbonate). The third portion (C) is filtered through a 3 μm Nuclepore® filter (47 mm—Polycarbonate) with the same method.

The emulsions were frozen in 100 ml balloon (−45° C. for 5 minutes) then freeze dried (0.2 mBar, for 72 hours).

Atmospheric pressure is restored by introducing a 35/65 mixture of $C_4F_{10}$ and air. The respective lyophilisates were dispersed in distilled water (10 ml). The so obtained microbubbles suspensions are analysed using a Coulter counter and the results are reported in the following table

|        | $D_{V50}$ | $D_N$ | $D_{V50}/D_N$ |
|--------|-----------|-------|---------------|
| Part A | 1.71      | 1.12  | 1.53          |
| Part B | 1.65      | 1.12  | 1.47          |
| Part C | 1.57      | 1.09  | 1.44          |

As shown by the above results, the additional filtration step allows to further reduce the dimension of the microbubbles and to reduce the respective size distribution.

Example 12

Example 1 has been repeated, by using 10 mg of a 7/3 (w/w) mixture of DSPC/DSTAP, at an agitation speed of 11000 rpm.

Characterization of emulsion droplets and microbubbles were as follows:

| Emulsion droplets | | Gas-filled microbubbles | | |
|---|---|---|---|---|
| $D_{V50}$ | $D_N$ | $D_{V50}$ | $D_N$ | >3 μm |
| 2.36 | 1.48 | 2.10 | 1.12 | 0.63 |

Example 13

The preparation of example 1 is repeated, by emulsifying the mixture at a speed of 10000 rpm (example 13a).

The same preparation is repeated, by further adding about 0.9 mg of DSPE-PEG2000 (about 8.3% of the total amount of dispersed phospholipids) to the initial aqueous suspension (example 13b).

No washing by centrifugation is performed on either the two preparations.

Table 10 shows the characterization of the two preparations, both of the emulsion and of the microbubbles suspension.

TABLE 10

|         | Emulsion | | Microbubbles | | | |
|---------|----------|--|-------------|--|--|--|
| Example | $D_{V50}$ (μm) | $D_N$ (μm) | $D_{V50}$ (μm) | $D_N$ (μm) | $D_{V50}/D_N$ | Conversion Yield (%) |
| 13a | 3.19 | 1.66 | 2.66 | 1.33 | 2.00 | 29.5 |
| 13b | 4.32 | 1.43 | 5.81 | 1.18 | 4.92 | 18.8 |

The above results show that with a concentration of DSPE-PEG of less than 10% by weight (with respect to the total amount of phospholipids), both conversion yields and size distribution of microbubbles are negatively affected.

Example 14

The preparation of example 11 is repeated, by replacing DPPS with the same amount of a 1:1 (w/w) mixture of DAPC/DPPS.

The resulting emulsion is divided in three portions of 10 ml, without washing it by centrifugation.

Aqueous suspensions of DSPE-PEG2000 and of DSPE-PEG5000 are separately prepared by dispersing 25 mg of the respective DSPE-PEG in 5 ml of a 10% mannitol solution under sonication (3 mm sonication probe, Branson 250 sonifier, output 30%, for 5 min).

An aliquot of 2.5 ml of a 10% mannitol solution is then added to a first portion of the emulsion (example 14a)

An aliquot of 2.5 ml of the prepared DSPE-PEG2000 suspension is added to a second portion of the emulsion (example 14b)

An aliquot of 2.5 ml of the prepared DSPE-PEG5000 suspension is added to a third portion of the emulsion (example 14c)

The three mixtures are heated at 60° C. under stirring for one hour. After cooling at room temperature, the size of microdroplets are determined by means of Malvern Mastersizer. Results are reported in table 11.

The emulsions are then freeze dried according to the procedure of example 11. Atmospheric pressure is restored by introducing a 35/65 mixture of $C_4F_{10}$ and air. The respective lyophilisates were dispersed in distilled water (10 ml). The so obtained microbubbles suspensions were analysed using a Coulter counter (see table 11).

Microbubble suspensions are then washed twice with distilled water by centrifugation (180 g/10 min) and lyophilized again according to the above procedure. The amount of DSPE-PEG in the dried composition is determined by means of HPLC-MS. Results are given in the following table 11.

TABLE 11

|         | Emulsion | | Microbubbles | | |
|---------|----------|--|-------------|--|--|
| Example | $D_{V50}$ (μm) | $D_N$ (μm) | $D_{V50}$ (μm) | $D_N$ (μm) | DSPE-PEG (% w/w) |
| 14a | 2.6 | 2.3 | 1.9 | 1.1 | 0.0 |
| 14b | 2.5 | 2.3 | 3.4 | 1.3 | 35.5 |
| 14c | 2.5 | 2.3 | 2.2 | 1.2 | 37.9 |

As inferable from the above results, the subsequent addition of a DSPE-PEG suspension to the formed emulsion allows introducing relatively high amounts of DSPE-PEG in the composition of the stabilizing layer (in this case more than 30% of the total weight of the phospholipids forming the stabilizing envelope), without negatively affecting the final properties of the microbubbles.

Similar results can be obtained with other PEG-modified phospholipids, in particular DSPE-PEG2000-Biotin or DSPE-PEG2000-Maleimide, and with peptide bearing phospholipids, in particular DSPE-PEG2000-maleimide-SATA-RGD4C. This latter peptide bearing phospholipid can be prepared according to known techniques, by reacting the RGD-4C peptide with SATA, deprotecting the thiol group of SATA and reacting the deprotected RGD4C-SATA with DSPE-PEG2000-maleimide. The preparation method described in "Development of EGF-conjugated liposomes for targeted delivery of boronated DNA-binding agents", by Bohl Kullberg et al., Bioconjugate chemistry 2002, 13, 737-743, (describing the insertion of a EGF protein in a DSPE-PEG-maleimide molecule), can be conveniently used.

Example 15

10 mg of a 1:1 (w/w) DPPS/DSPC mixture are added to about 10 ml of a 10% (w/w) mannitol aqueous solution.

The mixture is heated at 70° C. for 15 minutes and then cooled at room temperature (22° C.). Cyclooctane is added at a flow rate 0.2 mL/min through an inlet of a micromixer (standard slit interdigidital micro Mixer, housing SS 316Ti with nickel-on-copper inlay, 40 μm×300 μm, Institut für Microtechnik Mainz GmbH) to the aqueous phase circulating at 20 ml/min at room temperature, for a total amount of 7.4% (v/v) of organic solvent. Upon completion of the addition of the organic solvent, the emulsion is recirculated in the micromixer for additional 20 minutes.

The emulsion is then divided into five aliquots of 2 ml each and it is Introduced into five vials DIN8R. Four vials are sealed and heated for 30 minutes at temperatures of 60, 80, 100 and 120° C., respectively, as indicated in table 12, while the fifth is not heated.

The emulsions are then cooled to room temperature and the content of the five vials is subjected to lyophilization according to the following procedure. 1 ml of each emulsion is collected into a DIN8R vial and frozen at −5° C.; the temperature is lowered to −45° C. during 1 hour and the emulsion is then freeze-dried at −25° C. and 0.2 mbar during 12 hours (Telstar Lyobeta35 lyophilizer), with a final drying step at 30° C. and 0.2 mbar for 5 hours.

The lyophilized product is then exposed to an atmosphere containing 35% of perfluoro-n-butane and 65% of nitrogen and then dispersed in a volume of water twice than the initial one by gentle hand shaking. Table 12 shows the result of the characterization of the final suspension of microbubbles.

TABLE 12

| Heating | $D_{V50}$ | $D_N$ | $D_{V50}/D_N$ | Number of μbubbles per ml of emulsion |
|---|---|---|---|---|
| no heating | 10.45 | 1.63 | 6.41 | $5.34 \times 10^7$ |
| 60° C. | 4.85 | 1.32 | 3.67 | $7.83 \times 10^7$ |
| 80° C. | 5.34 | 1.29 | 4.14 | $8.51 \times 10^7$ |
| 100° C. | 6.96 | 1.66 | 4.19 | $4.92 \times 10^8$ |
| 120° C. | 3.05 | 1.50 | 2.03 | $8.69 \times 10^8$ |

From the above results, it appears that by subjecting the formed emulsion to a thermal treatment allows to narrow the size distribution of the final microbubble suspension, while also increasing the total number of microbubbles. In particular, by increasing the heating temperature above 100° C., it is possible to obtain a relatively narrow size distribution of microbubbles also in the absence of any washing step of the emulsion, as well as an increase of the total number of microbubbles in the suspension.

Example 16

Distilled water (10 ml) containing 10 mg of DPPS and 1 g of mannitol is heated to 70° C. during 15 minutes then cooled to room temperature. DPPE-MPB(1,2-Dipalmitoyl-sn-glycero-3-phosphoethanolamine-N-[4-(p-maleimidophenyl) butyramide] Na salt—Avanti Polar Lipids) is added (4.8% by weight—0.5 mg). This phospholipid is dispersed in the aqueous phase using a ultrasound bath (Branson 1210—3 minutes).

Perfluoroheptane (0.8 ml from Fluka) is emulsified in this aqueous phase (cooled with a ice bath) using a high speed homogenizer (Polytron® T3000, 15000 rpm, 1 minute).

The resulting emulsion showed a median diameter in volume ($D_{V50}$) of 2.3 μm and a mean diameter in number ($D_N$) of 2.1 μm as determined with a Malvern Mastersizer.

The emulsion is washed twice by centrifugation then resuspended in 9.5 ml of a 10% solution of mannitol in distilled water. The washed emulsion is frozen (−45° C., 5 minutes) then freeze dried (under 0.2 mBar, for 24 hours).

Atmospheric pressure is restored by introducing a 35/65 mixture of $C_4F_{10}$ and air. The lyophilisate is dispersed in distilled water (20 ml), microbubbles were washed once by centrifugation and then redispersed in 4 ml of an EDTA containing phosphate buffered saline (molar composition: 10 mM phosphate, 2.7 mM KCl, 137 mM NaCl, 10 mM EDTA), containing 3.4 mg of thioacetylated avidin, 400 μl of a hydroxylamine solution (13.92 mg in PBS 50 mM, pH: 7.5) were added to deprotect the thiol group of the thioacetylated avidin.

The suspension is stirred by inversion on a disk rotator (Fisher Scientific) for 2 hours. Then 150 μl of NaOH 1N were added.

The so obtained avidin-labelled microbubbles were washed twice with PBS by centrifugation (10000 rpm, 10 minutes, Sigma centrifuge 3K10). The microbubbles suspension obtained is analysed using a Coulter counter showing a $D_{V50}$ diameter of 1.6 μm and a $D_N$ of 1.2 μm.

The efficacy of targeted microbubbles composition was tested both in vitro and in vivo.

In Vitro Experiment:

To test the effective bonding of acetylated avidin to the surface of the microbubbles, two sets of fibrin containing wells were prepared. In the first set, only a fibrin surface is present. In the second set, the fibrin is pre-treated with a biotin-labelled antifibrin peptide (DX-278, disclosed in WO 02/055544). Microbubble suspensions prepared as above were added to the wells ($5 \times 10^8$ microbubbles/well). After 2 hours of incubation (upside down) and several washings, the fibrin surfaces in the two set of wells were observed by means of an optical microscope. While essentially no microbubble could be observed in the wells without the biotinylated antifibrin peptide, a massive coverage of microbubbles weas observed in the biotinylated antifibrin peptide containing wells.

In Vivo Experiment:

A thrombus is formed in the abdominal aorta of two rabbits by the $FeCl_3$ method (Lockyer et al, 1999, Journal of Cardiovascular Pharmacology, vol 33, pp 718-725).

Echo imaging is performed with an HDI 5000 ultrasound machine (Philips), pulse inversion mode, L7-4 probe, MI: 0.07.

A biotinylated antibody (CD41 specific for the GPIIB/IIIA receptor of activated platelets) is then injected intravenously to the two rabbit.

After 30 minutes, the microbubble suspension comprising avidin-labelled microbubbles is injected intravenously ($1 \times 10^9$ microbubbles/ml) in the first rabbit. Fifteen minutes after the injection, a strong opacification of the thrombus is observed for the suspension. This opacification is still visible after at least one hour from the injection.

The same amount of the microbubble suspension without avidin-labelled microbubbles is injected intravenously in the second rabbit. Only a light opacification of the thrombus is observed.

The invention claimed is:

1. A method for preparing a lyophilized matrix which, upon contact with an aqueous carrier liquid and a gas, is reconstitutable into a suspension of gas-filled microbubbles stabilized predominantly by a phospholipid, said method comprising the steps of:
   a) preparing an aqueous-organic emulsion comprising i) an aqueous medium including water, ii) an organic solvent substantially immiscible with water; iii) an emulsifying composition of amphiphilic materials comprising more than 50% by weight of a phospholipid and iv) a lyoprotecting agent, wherein the emulsion is substantially free of a structure builder selected from the group consisting of cholesterol and cyanacrylate and the temperature of the emulsion is lower than the boiling temperature of the organic solvent; and
   b) lyophilizing said emulsified mixture, to obtain a lyophilized matrix comprising said phospholipid.

2. The method of claim 1, wherein the step a) of preparing the emulsion comprises:
   a1) preparing a suspension by dispersing the emulsifying composition and the lyoprotective agent in the aqueous medium;
   a2) admixing the obtained suspension with the organic solvent;
   a3) submitting the mixture to controlled agitation, to obtain an emulsion.

3. The method of claim 1, wherein the organic solvent has a solubility in water of less than 10 g/l.

4. The method of claim 3, wherein the organic solvent has a solubility in water of 0.001 g/l or lower.

5. The method of claim 1, wherein the organic solvent is selected from the group consisting of branched or linear alkanes, alkenes, cyclo-alkanes, aromatic hydrocarbons, alkyl ethers, ketones, halogenated hydrocarbons, perfluorinated hydrocarbons and mixtures thereof.

6. The method of claim 5, wherein the solvent is selected from the group consisting of pentane, hexane, heptane, octane, nonane, decane, 1-pentene, 2-pentene, 1-octene, cyclopentane, cyclohexane, cyclooctane, 1-methyl-cyclohexane, benzene, toluene, ethylbenzene, 1,2-dimethylbenzene, 1,3-dimethylbenzene, di-butyl ether and di-isopropylketone, chloroform, carbon tetrachloride, 2-chloro-1-(difluoromethoxy)-1,1,2-trifluoroethane (enflurane), 2-chloro-2-(difluoromethoxy)-1,1,1-trifluoroethane (isoflurane), tetrachloro-1,1-difluoroethane, perfluoropentane, perfluorohexane, perfluoroheptane, perfluorononane, perfluorobenzene, perfluorodecalin, methylperfluorobutylether, methylperfluoroisobutylether, ethylperfluorobutylether, ethylperfluoroisobutylether and mixtures thereof.

7. The method of any of the preceding claims, wherein the amount of organic solvent is from about 1% to about 50% by volume with respect to the amount water.

8. The method of claim 1, wherein the lyoprotecting agent is selected from the group consisting of carbohydrates, sugar alcohols, polyglycols and mixtures thereof.

9. The method of claim 8, wherein the lyoprotecting agent is selected from the group consisting of glucose, galactose, fructose, sucrose, trehalose, maltose, lactose, amylose, amylopectin, cyclodextrins, dextran, inuline, soluble starch, hydroxyethyl starch (HES), erythritol, mannitol, sorbitol, polyethyleneglycols and mixtures thereof.

10. The method of claim 1, wherein the amount of lyoprotecting agent is from about 1% to about 25% by weight with respect to the weight of water.

11. The method of claim 1, wherein the phospholipid is selected from the group consisting of dilauroyl-phosphatidyl-choline (DLPC), dimyristoyl-phosphatidylcholine (DMPC), dipalmitoyl-phosphatidylcholine (DPPC), diarachidoyl-phosphatidylcholine (DAPC), distearoyl-phosphatidylcholine (DSPC), dioleoyl-phosphatidylcholine (DOPC), 1,2 Distearoyl-sn-glycero-3-Ethylphosphocholine (Ethyl-DSPC), dipentadecanoyl-phosphatidylcholine (DPDPC), 1-myristoyl-2-palmitoyl-phosphatidylcholine (MPPC), 1-palmitoyl-2-myristoyl-phosphatidylcholine (PMPC), 1-palmitoyl-2-stearoyl-phosphatidylcholine (PSPC), 1-stearoyl-2-palmitoyl-phosphatidylcholine (SPPC),), 1-palmitoyl-2-oleylphosphatidylcholine (POPC), 1-oleyl-2-palmitoyl-phosphatidylcholine (OPPC), dilauroyl-phosphatidylglycerol (DLPG) and its alkali metal salts, diarachidoylphosphatidyl-glycerol (DAPG) and its alkali metal salts, dimyristoylphosphatidylglycerol (DMPG) and its alkali metal salts, dipalmitoylphosphatidylglycerol (DPPG) and its alkali metal salts, distearoylphosphatidylglycerol (DSPG) and its alkali metal salts, dioleoyl-phosphatidylglycerol (DOPG) and its alkali metal salts, dimyristoyl phosphatidic acid (DMPA) and its alkali metal salts, dipalmitoyl phosphatidic acid (DPPA) and its alkali metal salts, distearoyl phosphatidic acid (DSPA), diarachidoylphosphatidic acid (DAPA) and its alkali metal salts, dimyristoyl-phosphatidylethanolamine (DMPE), dipalmitoylphosphatidylethanolamine (DPPE), distearoyl phosphatidyl-ethanolamine (DSPE), dioleylphosphatidyl-ethanolamine (DOPE), diarachidoylphosphatidylethanolamine (DAPE), dilinoleylphosphatidylethanolamine (DLPE), polyethyleneglycol modified dimyristoyl-phosphatidylethanolamine (DMPE-PEG), polyethyleneglycol modified dipalmitoylphosphatidylethanolamine (DPPE-PEG), polyethyleneglycol modified distearoyl phosphatidyl-ethanolamine (DSPE-PEG), polyethyleneglycol modified dioleylphosphatidyl-ethanolamine (DOPE-PEG), polyethyleneglycol modified diarachidoylphosphatidylethanolamine (DAPE-PEG), polyethyleneglycol modified dilinoleylphosphatidylethanolamine (DLPE-PEG), dimyristoyl phosphatidylserine (DMPS), diarachidoyl phosphatidylserine (DAPS), dipalmitoyl phosphatidylserine (DPPS), distearoylphosphatidylserine (DSPS), dioleylphosphatidylserine (DOPS), dipalmitoyl sphingomyelin (DPSP), and distearoylsphingomyelin (DSSP) and mixtures thereof.

12. The method of claim 1, wherein the emulsifying composition of amphiphilic materials comprises a phospholipid or an amphiphilic material bearing an overall net charge.

13. The method of claim 1, wherein the amount of phospholipid is from about 0.005% to about 1.0% by weight with respect to the total weight of the emulsified mixture.

14. The method of claim 13, wherein the amount of phospholipid is from 0.01% to 1.0% by weight with respect to the total weight of the emulsified mixture.

15. The method of claim 1, wherein the phospholipid includes a targeting ligand or a protective reactive group capable of reacting with a targeting ligand.

16. The method of claim 1, wherein the emulsion further contains an amphiphilic material selected from the group consisting of lysolipids; fatty acids and their respective salts with alkali or alkali metals; lipids bearing polymers; lipids bearing sulfonated mono- di-, oligo- or polysaccharides; lipids with ether or ester-linked fatty acids; polymerized lipids; diacetyl phosphate; diacetyl phosphate; stearylamine; ceramides; polyoxyethylene fatty acid esters; polyoxyethylene fatty alcohols; polyoxyethylene fatty alcohol ethers; polyoxyethylated sorbitan fatty acid esters; glycerol polyethylene glycol ricinoleate; ethoxylated soybean sterols; ethoxylated castor oil; ethylene oxide (EO) and propylene oxide (PO) block copolymers; sterol esters of sugar acids; esters of sugars with aliphatic acids; esters of glycerol with ($C_{12}$-$C_{24}$) dicarboxylic fatty acids and their respective salts with alkali or alkali-metal salts; saponins; long chain ($C_{12}$-$C_{24}$) alcohols; 6-(5-cholesten-3β-yloxy)-1-thio-β-D-galactopyranoside; digalactosyldiglyceride; 6-(5-cholesten-3β-yloxy)hexyl-6-amino-6-deoxy-1-thio-β-D-galactopyranoside; 6-(5-cholesten-3β-yloxy)hexyl-6-amino-6-deoxyl-1-thio-β-D-mannopyranoside; 12-(((7'-diethylaminocoumarin-3-yl)carbonyl)-methylamino)octadecanoic acid; N-[12-(((7'-diethylaminocoumarin-3-yl)carbonyl)methylamino)-octadecanoyl]-2-aminopalmitic acid; N-succinyldioleylphosphatidylethanolamine; 1-hexadecyl-2-palmitoylglycerophosphoethanolamine; palmitoylhomocysteine; alkylammonium salts comprising at least one ($C_{10}$-$C_{20}$) alkyl chain; tertiary or quaternary ammonium salts comprising at least one ($C_{10}$-$C_{20}$) acyl chain linked to the N-atom through a ($C_3$-$C_6$) alkylene bridge: and mixtures or combinations thereof.

17. The method of claim 1, wherein the aqueous-organic emulsion of step a) is subjected to a washing step before the lyophilizing step b).

18. The method of claim 1, wherein the aqueous-organic emulsion of step a) is subjected to a microfiltration step before the lyophilizing step b).

19. The method of claim 1 which further comprises adding an aqueous suspension comprising a further amphiphilic compound to the aqueous-organic emulsion obtained according to step a), before the lyophilization step b), thus obtaining a second aqueous-organic emulsion comprising said further amphiphilic compound.

20. The method of claim 19 which further comprises heating the mixture of said aqueous suspension and of said aqueous-organic emulsion.

21. The method of claim 20, wherein said mixture is heated at a temperature of from about 40° C. to about 80° C.

22. The method of claim 21, wherein said amphiphilic compound is a PEG-modified phospholipid, a PEG-modified phospholipid bearing a reactive moiety or a PEG-modified phospholipid bearing a targeting ligand.

23. The method of claim 1 which further comprises, before the lyophilization step b), subjecting the aqueous-organic emulsion to a controlled heating.

24. The method of claim 19 which further comprises, before the lyophilization step b), subjecting the aqueous-organic emulsion to a controlled heating.

25. The method of any one of claim 23 or 24, wherein said controlled heating is effected at a temperature of from about 60° C. to 125° C.

26. The method of any one of claim 23 or 24, wherein said controlled heating is effected at a temperature of from about 60° C. to 125° C. and said emulsion is contained in a sealed vial.

27. A method for preparing an injectable contrast agent comprising a liquid aqueous suspension of gas-filled microbubbles stabilized predominantly by phospholipids, which comprises:
 a) preparing an aqueous-organic emulsion comprising i) an aqueous medium including water, ii) an organic solvent substantially immiscible with water; iii) an emulsifying composition of amphiphilic materials comprising more than 50% by weight of a phospholipid and iv) a lyoprotecting agent, wherein the emulsion is substantially free of a structure builder selected from the group consisting of cholesterol and cyanacrylate and the temperature of the emulsion is lower than the boiling temperature of the organic solvent;
 b) lyophilizing said emulsified mixture, to obtain a lyophilized matrix comprising said phospholipids;
 c) contacting said lyophilized matrix with a biocompatible gas; and
 d) reconstituting said lyophilized matrix by dissolving it in a physiologically acceptable aqueous carrier liquid, to obtain a suspension of gas-filled microbubbles stabilized predominantly by said phospholipid.

28. The method of claim 27, wherein the biocompatible gas is selected from the group consisting of air; nitrogen; oxygen; carbon dioxide; hydrogen; nitrous oxide; inert gases; a low molecular weight hydrocarbon, including a ($C_1$-$C_7$) alkane, a ($C_4$-$C_7$) cycloalkane, a ($C_2$-$C_7$) alkene and a ($C_2$-$C_7$) alkyne; an ether; a ketone; an ester; a halogenated ($C_1$-$C_7$) hydrocarbon, ketone; ether; and a mixture of any of the foregoing.

29. The method of claim 28, wherein the halogenated hydrocarbon gas is a perfluorinated hydrocarbon or sulfur hexafluoride.

30. The method of claim 29, wherein the perfluorinated hydrocarbon gas is selected from the group consisting of perfluoromethane, perfluoroethane, a perfluoropropane, a perfluorobutane, a perfluoropentane, a perfluorohexane, a perfluoroheptane; perfluoropropene, a perfluorobutene, perfluorobutadiene, perfluorobut-2-yne, perfluorocyclobutane, perfluoromethylcyclobutane, a perfluorodimethylcyclobutane, a perfluorotrimethylcyclo-butane, perfluorocyclopentane, perfluoromethylcyclopentane, a perfluorodimethylcyclo-pentane, perfluorocyclohexane, perfluoromethylcyclohexane, perfluoromethylcyclohexane and mixtures thereof.

31. The method of claim 27, wherein said microbubbles have a number mean diameter ($D_N$) of less than 1.70 μm and a volume median diameter ($D_{V50}$) such that the $D_{V50}/D_N$ ratio is of about 2.00 or lower.

32. The method of claim 31, wherein said microbubbles have a $D_N$ value of 1.60 μm or lower, preferably of 1.50 μm or lower, more preferably of 1.30 μm or lower.

33. The method of claim 32, wherein said microbubbles have a $D_{V50}/D_N$ ratio of about 1.80 or lower, preferably of about 1.60 or lower, more preferably of about 1.50 or lower.

34. The method of claim 27, wherein the step a) of preparing the emulsion comprises:
 a1) preparing a suspension by dispersing the emulsifying composition and the lyoprotective agent in the aqueous medium;
 a2) admixing the obtained suspension with the organic solvent;
 a3) submitting the mixture to controlled agitation, to obtain an emulsion.

35. The method of claim 27, wherein the organic solvent has a solubility in water of less than 10 g/l.

36. The method of claim 35, wherein the organic solvent has a solubility in water of less than 0.001 g/l.

37. The method of claim 27, wherein the organic solvent is selected from the group consisting of branched or linear alkanes, alkenes, cyclo-alkanes, aromatic hydrocarbons, alkyl ethers, ketones, halogenated hydrocarbons, perfluorinated hydrocarbons and mixtures thereof.

38. The method of claim 37, wherein the solvent is selected from the group consisting of pentane, hexane, heptane, octane, nonane, decane, 1-pentene, 2-pentene, 1-octene, cyclopentane, cyclohexane, cyclooctane, 1-methyl-cyclohexane, benzene, toluene, ethylbenzene, 1,2-dimethylbenzene, 1,3-dimethylbenzene, di-butyl ether and di-isopropylketone, chloroform, carbon tetrachloride, 2-chloro-1-(difluoromethoxy)-1,1,2-trifluoroethane (enflurane), 2-chloro-2-(difluoromethoxy)-1,1,1-trifluoroethane (isoflurane), tetrachloro-1,1-difluoroethane, perfluoropentane, perfluorohexane, perfluoroheptane, perfluorononane, perfluorobenzene, perfluorodecalin, methylperfluorobutylether, methylperfluoroisobutylether, ethylperfluorobutylether, ethylperfluoroisobutylether and mixtures thereof.

39. The method of claim 27, wherein the amount of organic solvent is from about 1% to about 50% by volume with respect to the amount water.

40. The method of claim 27, wherein the lyoprotecting agent is selected from the group consisting of carbohydrates, sugar alcohols, polyglycols and mixtures thereof.

41. The method of claim 40, wherein the lyoprotecting agent is selected from the group consisting of glucose, galactose, fructose, sucrose, trehalose, maltose, lactose, amylose, amylopectin, cyclodextrins, dextran, inuline, soluble starch, hydroxyethyl starch (HES), erythritol, mannitol, sorbitol, polyethyleneglycols and mixtures thereof.

42. The method of claim 27, wherein the amount of lyoprotecting agent is from about 1% to about 25% by weight with respect to the weight of water.

43. The method of claim 27, wherein the phospholipid is selected from the group consisting of dilauroyl-phosphatidylcholine (DLPC), dimyristoyl-phosphatidylcholine (DMPC), dipalmitoyl-phosphatidylcholine (DPPC), diarachidoyl-phosphatidylcholine (DAPC), distearoyl-phosphatidylcholine (DSPC), dioleoyl-phosphatidylcholine (DOPC), 1,2 Distearoyl-sn-glycero-3-Ethylphosphocholine (Ethyl-DSPC), dipentadecanoyl-phosphatidylcholine (DPDPC), 1-myristoyl-2-palmitoyl-phosphatidylcholine (MPPC), 1-palmitoyl-2-myristoyl-phosphatidylcholine (PMPC), 1-palmitoyl-2-stearoyl-phosphatidylcholine (PSPC), 1-stearoyl-2-palmitoyl-phosphatidylcholine (SPPC), 1-palmitoy-2-oleylphosphatidylcholine (POPC), 1-oleyl-2-palmitoyl-phosphatidylcholine (OPPC), dilauroyl-phosphatidylglycerol (DLPG) and its alkali metal salts, diarachidoylphosphatidyl-glycerol (DAPG) and its alkali metal salts, dimyristoylphosphatidylglycerol (DMPG) and its alkali metal salts, dipalmitoylphosphatidylglycerol (DPPG) and its alkali metal salts, distearoylphosphatidylglycerol (DSPG) and its alkali metal salts, dioleoyl-phosphatidylglycerol (DOPG) and its alkali metal salts, dimyristoyl phosphatidic acid (DMPA) and its alkali metal salts, dipalmitoyl phosphatidic acid (DPPA) and its alkali metal salts, distearoyl phosphatidic acid (DSPA), diarachidoylphosphatidic acid (DAPA) and its alkali metal salts, dimyristoyl-phosphatidyle-thanolamine (DMPE), dipalmitoylphosphatidylethanolamine (DPPE), distearoyl phosphatidyl-ethanolamine (DSPE), dioleylphosphatidyl-ethanolamine (DOPE), diarachidoylphosphatidylethanolamine (DAPE), dilinoleylphosphatidylethanolamine (DLPE), polyethyleneglycol modified dimyristoyl-phosphatidylethanolamine (DMPE-PEG), polyethyleneglycol modified dipalmitoylphosphatidylethanolamine (DPPE-PEG), polyethyleneglycol modified distearoyl phosphatidyl-ethanolamine (DSPE-PEG), polyethyleneglycol modified dioleylphosphatidyl-ethanolamine (DOPE-PEG), polyethyleneglycol modified diarachidoylphosphatidylethanolamine (DAPE-PEG), polyethyleneglycol modified dilinoleylphosphatidylethanolamine (DLPE-PEG), dimyristoyl phosphatidylserine (DMPS), diarachidoyl phosphatidylserine (DAPS), dipalmitoyl phosphatidylserine (DPPS), distearoylphosphatidylserine (DSPS), dioleoylphosphatidylserine (DOPS), dipalmitoyl sphingomyelin (DPSP), and distearoylsphingomyelin (DSSP) and mixtures thereof.

44. The method of claim 27, wherein the emulsifying composition of amphiphilic materials comprises a phospholipid or an amphiphilic material bearing an overall net charge.

45. The method of claim 27, wherein the amount of phospholipid is from about 0.005% to about 1.0% by weight with respect to the total weight of the emulsified mixture.

46. The method of claim 45, wherein the amount of phospholipid is from 0.01% to 1.0% by weight with respect to the total weight of the emulsified mixture.

47. The method of claim 27, wherein the phospholipid includes a targeting ligand or a protective reactive group capable of reacting with a targeting ligand.

48. The method of claim 27, wherein the emulsion further contains an amphiphilic material selected from the group consisting of lysolipids; fatty acids and their respective salts with alkali or alkali metals; lipids bearing polymers; lipids bearing sulfonated mono-di-, oligo- or polysaccharides; lipids with ether or ester-linked fatty acids; polymerized lipids; diacetyl phosphate; dicetyl phosphate; stearylamine; ceramides; polyoxyethylene fatty acid esters; polyoxyethylene fatty alcohols; polyoxyethylene fatty alcohol ethers; polyoxyethylated sorbitan fatty acid esters; glycerol polyethylene glycol ricinoleate; ethoxylated soybean sterols; ethoxylated castor oil; ethylene oxide (EO) and propylene oxide (PO) block copolymers; sterol esters of sugar acids; esters of sugars with aliphatic acids; esters of glycerol with ($C_{12}$-$C_{24}$) dicarboxylic fatty acids and their respective salts with alkali or alkali-metal salts; saponins; long chain ($C_{12}$-$C_{24}$) alcohols; 6-(5-cholesten-3β-yloxy)-1-thio-β-D-galactopyranoside; digalactosyldiglyceride; 6-(5-cholesten-3β-yloxy)hexyl-6-amino-6-deoxy-1-thio-β-D-galactopyranoside; 6-(5-cholesten-3β-yloxy)hexyl-6-amino-6-deoxyl-1-thio-β-D-mannopyranoside; 12-(((7'-diethylaminocoumarin-3-yl)carbonyl)-methylamino)octadecanoic acid; N-[12-(((7'-diethylaminocoumarin-3-yl)carbonyl)methylamino)-octadecanoyl]-2-aminopalmitic acid; N-succinyldioleylphosphatidylethanolamine; 1-hexadecyl-2-palmitoylglycerophosphoethanolamine; palmitoylhomocysteine; alkylammonium salts comprising at least one ($C_{10}$-$C_{20}$) alkyl chain; tertiary or quaternary ammonium salts comprising at least one ($C_{10}$-$C_{20}$) acyl chain linked to the N-atom through a ($C_3$-$C_6$) alkylene bridge: and mixtures or combinations thereof.

49. The method of claim 27, wherein the aqueous-organic emulsion of step a) is subjected to a washing or microfiltration step before the lyophilizing step b).

50. The method of claim 27 which further comprises adding an aqueous suspension comprising a further amphiphilic compound to the aqueous-organic emulsion obtained according to step a), before the lyophilization step b), thus obtaining a second aqueous-organic emulsion comprising said further amphiphilic compound.

51. The method of claim 50 which further comprises heating the mixture of said aqueous suspension and of said aqueous-organic emulsion.

52. The method of claim 51, wherein said mixture is heated at a temperature of from about 40° C. to about 80° C.

53. The method of claim 50, wherein said amphiphilic compound is a PEG-modified phospholipid, a PEG-modified phospholipid bearing a reactive moiety or a PEG-modified phospholipid bearing a targeting ligand.

54. The method of claim 27 which further comprises, before the lyophilization step b), subjecting the aqueous-organic emulsion to a controlled heating.

55. The method of claim 50 which further comprises, before the lyophilization step b), subjecting the aqueous-organic emulsion to a controlled heating.

56. The method of any one of claim 54 or 55, wherein said controlled heating is effected at a temperature of from about 60° C. to 125° C.

57. The method of any one of claim 54 or 55, wherein said controlled heating is effected at a temperature of from about 60° C. to 125° C. and said emulsion is contained in a sealed vial.

* * * * *